United States Patent
Kurihara et al.

(10) Patent No.: US 11,365,194 B2
(45) Date of Patent: Jun. 21, 2022

(54) ANALGESIC DRUG USING PAC1 RECEPTOR ANTAGONISTIC DRUG

(71) Applicants: KAGOSHIMA UNIVERSITY, Kagoshima (JP); SHOWA UNIVERSITY, Tokyo (JP)

(72) Inventors: Takashi Kurihara, Kagoshima (JP); Ichiro Takasaki, Toyama (JP); Naoki Toyooka, Toyama (JP); Hiroaki Gouda, Tokyo (JP)

(73) Assignees: KAGOSHIMA UNIVERSITY, Kagoshima (JP); SHOWA UNIVERSITY, Tokyo (JP)

( * ) Notice: Subject to any disclaimer, the term of this patent is extended or adjusted under 35 U.S.C. 154(b) by 106 days.

(21) Appl. No.: 16/650,133

(22) PCT Filed: Sep. 27, 2018

(86) PCT No.: PCT/JP2018/035831
§ 371 (c)(1),
(2) Date: Mar. 24, 2020

(87) PCT Pub. No.: WO2019/065794
PCT Pub. Date: Apr. 4, 2019

(65) Prior Publication Data
US 2021/0188841 A1    Jun. 24, 2021

(30) Foreign Application Priority Data

Sep. 27, 2017  (JP) .............................. JP2017-186447

(51) Int. Cl.
*C07D 471/04*  (2006.01)
*C07D 403/14*  (2006.01)

(52) U.S. Cl.
CPC ......... *C07D 471/04* (2013.01); *C07D 403/14* (2013.01)

(58) Field of Classification Search
CPC .................................................. C07D 471/04
See application file for complete search history.

(56) References Cited

U.S. PATENT DOCUMENTS

2019/0008839 A1    1/2019   Martinez et al.

FOREIGN PATENT DOCUMENTS

WO       2017/029202 A1   2/2017

OTHER PUBLICATIONS

EPO, "Extended European Search Report", issued in connection with corresponding EP application No. 18862130.4, dated Jan. 11, 2021 (10 pages).

Yokai et al., "Spinal astrocytic activation contributes to both induction and maintenance of pituitary adenylate cyclase-activating polypeptide type 1 receptor-induced long-lasting mechanical allodynia in mice", Molecular Pain, 2016, vol. 12, pp. 1-13.

Mabuchi et al., "Pituitary Adenylate Cyclase-Activating Polypeptide is Required for the Development of Spinal Sensitization and Induction of Neuropathic Pain", Journal of Neuroscience, 2004, vol. 24, No. 33, pp. 7283-7291.

Ohnou et al., "Pituitary adenylate cyclase-activating polypeptide type 1 receptor signaling evokes long-lasting nociceptive behaviors through the activation of spinal astrocytes in mice", Journal of Pharmacological Sciences, 2016, vol. 130, pp. 194-203.

Takasaki,"Creation of new PAC1 receptor antagonists utilizing IT drug discovery—Aiming for the development of drugs for treating chronic pain including migraine—", Research Achievement Report by Young Researcher Supported by Grant from Hokuriku Bank, Ltd., 2015, 15 Pages, English Translation.

Shi et al.,"An Efficient and Clean Synthesis of Pyrido[2,3-d]pyrimidine-4,7-dione Derivatives in Aqueous Media", J. Heterocyclic Chem., 2009, vol. 46, pp. 1331-1334.

Tu et al., "New potential inhibitors of cyclin-dependent kinase 4: Design and synthesis of pyrido[2,3-d]pyrimidine derivatives under microwave irradiation", Bioorganic & Medicinal Chemistry Letters, 2006, vol. 16, pp. 3578-3581.

(Continued)

*Primary Examiner* — Brian E McDowell
(74) *Attorney, Agent, or Firm* — Lucas & Mercanti, LLP

(57) ABSTRACT

This invention relates to an analgesic drug comprising a compound represented by the following formula (I) or (II),

[Formula 1]

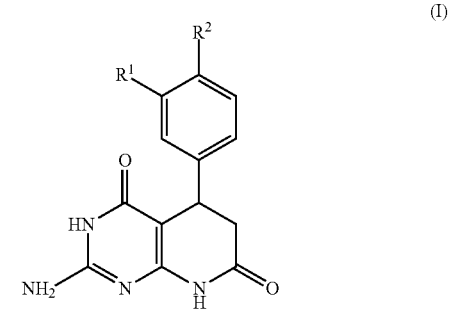

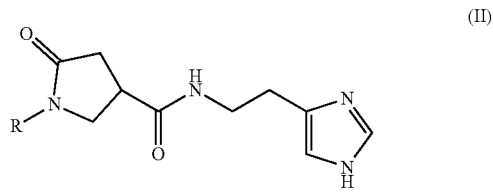

wherein $R^1$ is a $C_{1-6}$-alkoxy group or a $C_{1-6}$-haloalkoxy group; $R^2$ is a hydrogen atom; and R is an indazolyl group substituted with a halogen atom; a substituted or unsubstituted phenyl group; a pyrazolyl group; or a substituted or unsubstituted aralkyl group; or a salt thereof, or a solvate thereof.

3 Claims, 12 Drawing Sheets

(56) References Cited

OTHER PUBLICATIONS

Nagashima et al., "Development of small molecule antagonist for PAC1 receptor aimed at drug discovery of novel analgesics-1," Lecture abstracts of the 35th Symposium on Medicinal Chemistry, 2017, pp. 229.
Database Registry, Retrieved from STN international, 2015, 2 pages.
Ogashi et al., "Development of small molecule antagonist for PAC1 receptor aimed at drug discovery of novel analgesics-2," Lecture abstracts of the 35th Symposium on Medicinal Chemistry, 2017, pp. 116.
International Search report for Corresponding International Application No. PCT/JP2018/035831 (dated Dec. 18, 2018) (3 Pages).

ANALGESIC DRUG USING PAC1 RECEPTOR ANTAGONISTIC DRUG

CROSS-REFERENCE TO RELATED APPLICATIONS

This application is a 371 of PCT/JP2018/035831, filed Sep. 27, 2018, which claims benefit of Japanese Patent Application No. 2017-186447, filed Sep. 27, 2017.

TECHNICAL FIELD

The present invention relates to an analgesic drug using a PAC receptor antagonistic drug.

BACKGROUND ART

Pain which needs treatment can be pathophysiologically classified into inflammatory pain and neuropathic pain. Inflammatory pain is nociceptive pain through nociceptors, and is pain caused by an inflammatory mediator released at the site of tissue damage. Meanwhile, neuropathic pain is defined as pain caused by a lesion or disease of the somatosensory nervous system. The excitement of nociceptors may not be involved in neuropathic pain. Plastic changes in peripheral or central nervous system are often involved in neuropathic pain, so that the refractory degree is also high, resulting in difficulty in the treatment.

Various pain diseases are expected to increase with the aging of the population in advanced countries. The Congress of the United States adopted declaration in which the ten years from 2001 to 2010 was called "The Decade of Pain Control and Research" for the following reasons. Research on actual conditions all over the United States estimated that patients suffering from severe chronic pain reached 9% of the adult population, and that the loss of the social economy due to the waste of medical expenses due to ineffective treatment and doctor shopping, difficulty in working due to pain, nursing care expenses, and the like reached 65 billion dollars (around 8 trillion yen) per year. In Japan, it is also estimated that the number of patients suffering chronic pain now exceeds 20 million. Thus, it is socially imperative to establish effective drug treatment for intractable pain.

Although NSAIDs (non-steroidal anti-inflammatory drugs) and opioids (narcotic analgesic drugs) have been mainly used as analgesic drugs now, especially patients with chronic pain use these analgesic drugs over a long period of time, resulting in suffering significant various adverse actions, and the qualities of life of pain patients are thus markedly reduced. Therefore, the development of a new analgesic drug with high effectiveness which can be used over a long period of time has been strongly required.

Pain control with NSAIDs or opioids has many adverse actions such as stomach disorder and nephropathy (the above caused by mainly NSAIDs); and constipation, nausea vomiting, dependence and respiratory depression (caused by mainly opioids), and often has an insufficient analgesic effect on neuropathic pain, and such pain control needs to be performed with the adverse actions accepted. Therefore, a new therapeutic drug for pain with different mechanisms of action from these analgesic drugs has been desired.

PACAP (Pituitary Adenylate Cyclase-Activating Polypeptide) is a neuropeptide which was originally isolated from ovine hypothalamus based on its ability to stimulate adenylate cyclase in rat anterior pituitary cell cultures and structurally determined in 1989, and causes mechanical pain hypersensitivity (mechanical allodynia: the phenomenon of feeling pain even though the patient is only touched) through spinal PAC1 receptors (Non Patent Literature 1). However, it is unclear what type of pain PACAP is involved in clinically (in a human).

It is suggested that PACAP is involved in peripheral neuropathic (spinal neuropathic) pain (SNL model) at the level of animal experiments (mice and rats) (Non Patent Literature 2). However, it is unclear which PACAP receptor is involved (PACAP receptors have at least three types, which are PAC1, VPAC1 and VPAC2).

Non Patent Literature 3 discloses that the compounds PA-8 and PA-9, which were selected from the existing compound database in which 4 million or more items are registered, have PAC1 receptor antagonistic action. However, the chemical structure of PA-8 is not clarified, and the analgesic action thereof is not examined.

Non Patent Literature 4 shows the structures of the compounds PA-8 and PA-9 and also shows that these compounds have analgesic effect.

The compound PA-8 is a compound represented by the following formula (A):

[Formula 1]

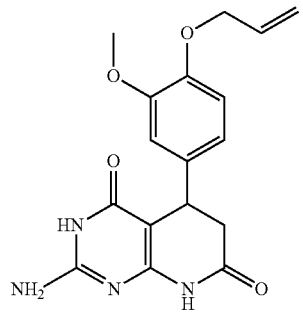

The compound PA-9 is a compound represented by the following formula (B):

[Formula 2]

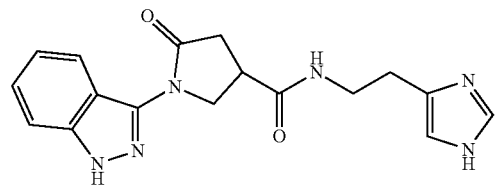

These compounds are common in that the compounds each have a nitrogen-containing heterocyclic structure containing two or more nitrogen atoms and a lactam structure.

Although Non Patent Literatures 5 and 6 describe a pyrido[2,3-d]pyrimidine-4,7-dione derivative represented by the following formula (I'):

[Formula 3]

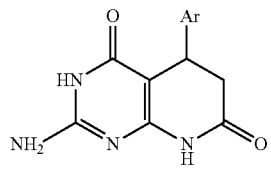

wherein Ar is a substituted phenyl group and a method of synthesizing the same, Non Patent Literatures 5 and 6 do not mention PAC receptor antagonistic action and analgesic action.

CITATION LIST

Non Patent Literature

[Non Patent Literature 1] Yokai et al. Mol. Pain 2016, 12, 1-13.
[Non Patent Literature 2] Mabuchi et al., J Neurosci 2004, 24, 7283-7291.
[Non Patent Literature 3] Journal of Pharmacological Sciences. Volume 130, Issue 3, Supplement, Page S236 (March 2016)
[Non Patent Literature 4] Research Achievement Report by Young Researcher Supported by Grant from HOKURIKU BANK, LTD., 2015
[Non Patent Literature 5] Shi, D. Q. et al. J. Heterocyclic Chem. 2009, 46, 1331-1334
[Non Patent Literature 6] Tu, S. et al., Bioorg. Med. Chem. Lett. 2006, 16.3578-3581

SUMMARY OF INVENTION

Technical Problem

An object of the present invention is to provide a new therapeutic drug for pain having an action mechanism different from NSAIDs or opioids.

Solution to Problem

The present inventors have found PAC1 receptor antagonistic drug candidate compounds from the existing compound database to achieve the object. The present inventors have further noticed that the compounds PA-8 and PA-9 among the candidate compounds are common in that the compounds have a nitrogen-containing heterocyclic structure containing two or more nitrogen atoms and a lactam structure, and performed the structure development of the compounds PA-8 and PA-9. The present inventors have succeeded in synthesizing compounds which exhibit an effect equivalent or superior to the compound PA-8 or PA-9, which is a basic compound, and completed the present invention.

More specifically, the present invention will be summarized as follows.

(1) A compound represented by the following formula (I),

[Formula 4]

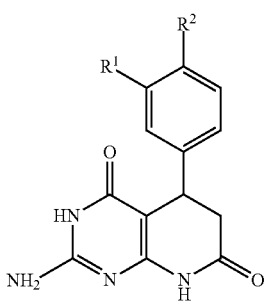

wherein $R^1$ is a $C_{1-6}$-alkoxy group or a $C_{1-6}$-haloalkoxy group; and $R^2$ is a hydrogen atom; or a salt thereof, or a solvate thereof.

(2) The compound according to (1) or a salt thereof, or a solvate thereof, wherein $R^1$ is an ethoxy group or a trifluoromethoxy group in the formula (I).

(3) An analgesic drug comprising a compound according to (1) or (2), a salt thereof, or a solvate thereof.

(4) The analgesic drug according to (3) for treating and/or preventing a disease or symptom selected from the group consisting of neuropathic pain, pain associated with cancer chemotherapy, diabetic neuralgia, diabetic peripheral neuropathic pain, and migraine.

(5) An analgesic drug comprising a compound represented by the following formula (II),

[Formula 5]

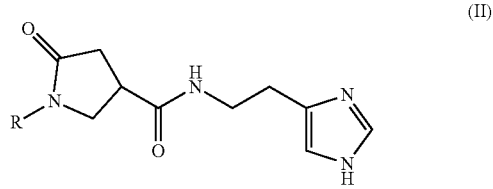

wherein R is an indazolyl group substituted with a halogen atom; a substituted or unsubstituted phenyl group; a pyrazolyl group; or a substituted or unsubstituted aralkyl group; or a salt thereof, or a solvate thereof.

(6) The analgesic drug according to (5), wherein R is an indazolyl group substituted with a halogen atom in the formula (II).

(7) The analgesic drug according to (5), wherein R is an indazolyl group substituted with a chlorine atom in the formula (II).

(8) The analgesic drug according to any one of (5) to (7) for treating and/or preventing a disease or symptom selected from the group consisting of neuropathic pain, pain associated with cancer chemotherapy, diabetic neuralgia, diabetic peripheral neuropathic pain, and migraine.

(9) A compound represented by the following formula (IIa),

[Formula 6]

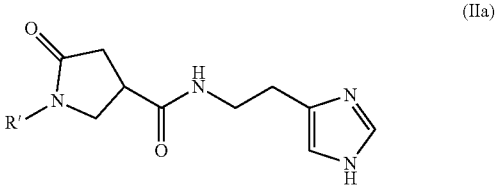

wherein R' is an indazolyl group substituted with a halogen atom; a phenyl group which may be substituted with a methyl group, a fluorine atom, a methoxy group, a cyano group or a hydroxyl group; a pyrazolyl group; or a substituted aralkyl group;
or a salt thereof, or a solvate thereof.

(10) The compound according to (9) or a salt thereof, or a solvate thereof, wherein R' is an indazolyl group substituted with a halogen atom in the formula (IIa).

(11) The compound according to (9) or a salt thereof, or a solvate thereof, wherein R' is an indazolyl group substituted with a chlorine atom in the formula (IIa).

Advantageous Effects of Invention

A compound of the present invention has a nitrogen-containing heterocyclic structure containing two or more nitrogen atoms and a lactam structure, and is useful as an analgesic drug. The analgesic drug is a new therapeutic drug for pain and has an action mechanism different from NSAIDs or opioids.

By use of the analgesic drug of the present invention, the pain treatment can be performed which avoids adverse actions such as peptic ulcer found at the time of using an NSAID and constipation found at the time of using an opioid. Since a therapeutic effect can be expected in both of inflammatory pain and neuropathic pain, the necessity for combined use of multi-drugs can be decreased, and therefore, the occurrence of unexpected adverse actions can be avoided. Moreover, since a therapeutic effect can be expected in both peripheral neuropathic pain and pain associated with cancer chemotherapy, the improvement in the qualities of life of patients with intractable cancer pain can be expected.

DESCRIPTION OF EMBODIMENTS

Figure 1:
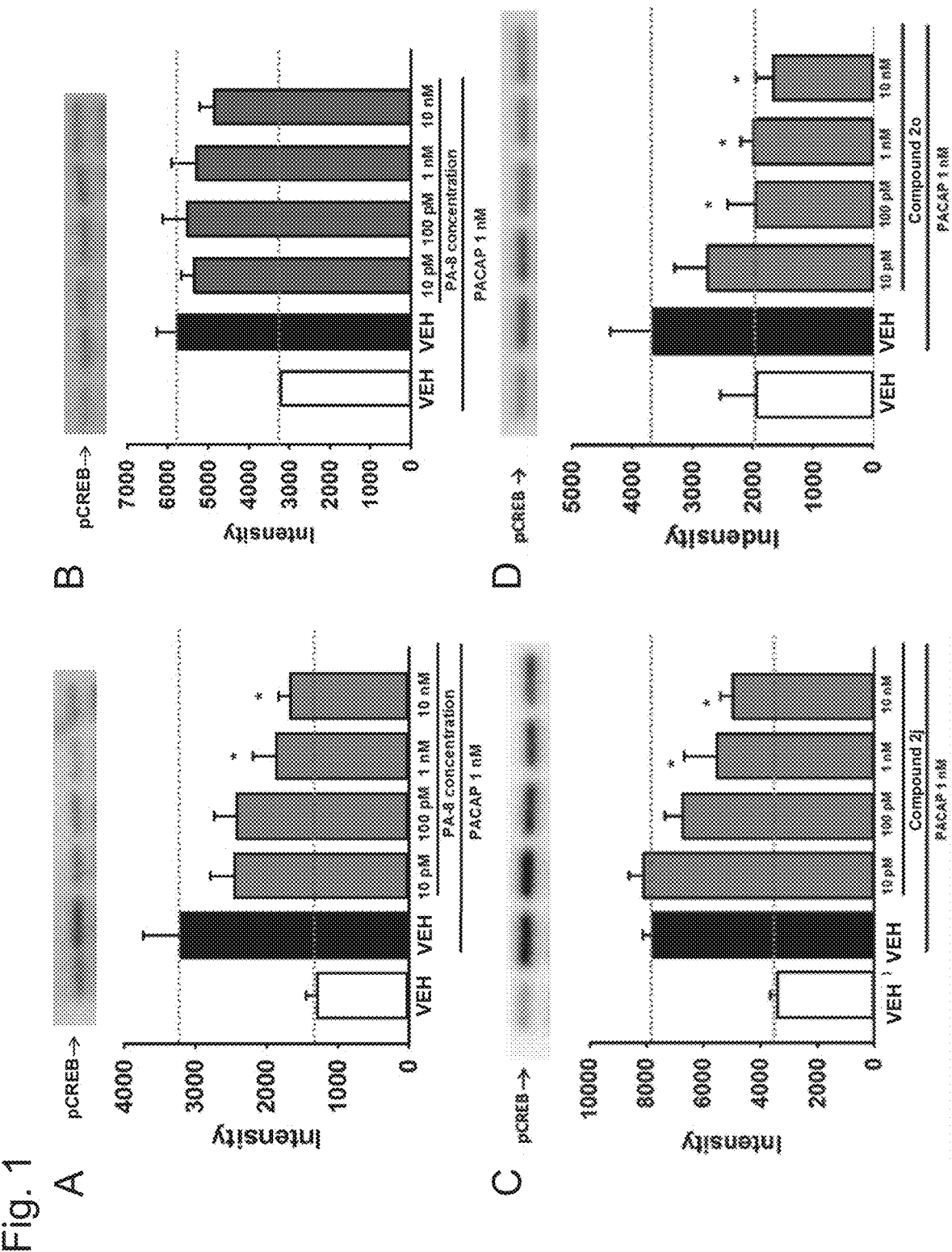
FIG. 1 shows the evaluation of PA-8 and derivatives thereof (compounds 2j and 2o) using PACAP receptor-expressing cells.

The present invention will be described in detail hereinafter.

Examples of the $C_{1-6}$-alkoxy group represented by $R^1$ in the formula (I) include a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, a cyclopropyloxy group, a cyclobutyloxy group, a cyclopentyloxy group and a cyclohexyloxy group.

Examples of the $C_{1-6}$-haloalkoxy group represented by R in the formula (I) include a trifluoromethoxy group.

An indazolyl group substituted with a halogen atom and represented by R in the formula (II) is not particularly limited as long as it is an indazolyl group substituted with at least one halogen atom selected from fluorine atoms, chlorine atoms, bromine atoms and iodine atoms (preferably chlorine atom). However, preferable examples thereof include a 3-indazolyl group substituted with at least one chlorine atom.

Examples of the aralkyl group represented by R in the formula (II) include a benzyl group and a phenethyl group.

The phenyl and aralkyl group represented by R in the formula (II) may be substituted with one or more substituents selected from a $C_{1-6}$-alkyl group (for example, a methyl group, an ethyl group, a propyl group, an isopropyl group, a butyl group, an isobutyl group, a sec-butyl group (1-methylpropyl group), a tert-butyl group, a pentyl group, an isopentyl group, 1-ethylpropyl group, a hexyl group, a cyclopropyl group, a cyclobutyl group, a cyclopentyl group and a cyclohexyl group), a $C_{1-6}$-alkoxy group (for example, a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, a cyclopropyloxy group, a cyclobutyloxy group, a cyclopentyloxy group and a cyclohexyloxy group), a methylenedioxy group, a $C_{2-6}$-alkenyloxy group, an aralkyloxy group (for example, a benzyloxy group, a 4-methylbenzyloxy group, a 3-methylbenzyloxy group, a 2-methylbenzyloxy group, a 4-fluorobenzyloxy group, a 3-fluorobenzyloxy group, a 4-chlorobenzyloxy group and a 3-chlorobenzyloxy group), a halogen atom (such as a fluorine atom, a chlorine atom, a bromine atom and an iodine atom), a $C_{1-6}$-haroalkyl group, a $C_{1-6}$-haroalkoxy group, a substituted or unsubstituted phenyl group, an acyl group (for example, a $C_{1-6}$-aliphatic acyl group such as a formyl group, an acetyl group, a propanoyl group, a butanoyl group, a pentanoyl group and a hexanoyl group; and an aroyl group such as a benzoyl group and a toluoyl group), an acyloxy group (for example, a $C_{1-6}$-aliphatic acyloxy group such as a formyloxy group, an acetoxy group, a propanoyloxy group, a butanoyloxy group, a pentanoyloxy group and a hexanoyloxy group; and an aroyloxy group such as a benzoyloxy group and a toluoyloxy group), a hydroxyl group, a carboxyl group, an acetamido group, a carbamoyl group, a cyano group, a nitro group, and the like.

Among the compounds represented by the formula (I), compounds wherein $R^1$ is a $C_{1-6}$-haroalkoxy group, for example, a trifluoromethoxy group are preferable.

Among the compounds represented by the formula (II), compounds wherein R is a 3-indazolyl group substituted with at least one chlorine atom are preferable.

Among the compounds represented by the formula (II), the compounds represented by the following formula (IIa).

[Formula 7]

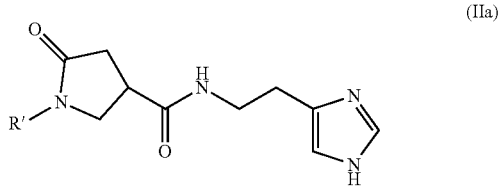

(IIa)

wherein R' is an indazolyl group substituted with a halogen atom; a phenyl group which may be substituted with a methyl group, a fluorine atom, a methoxy group, a cyano group or a hydroxyl group; a pyrazolyl group; or a substituted aralkyl group:
are novel compounds.

The salt of a compound represented by the formula (I) or (II) is preferably a pharmaceutically acceptable salt, and examples of the salt include a salt of the compound with an inorganic acid such as hydrochloric acid, sulfuric acid, phosphoric acid, hydrobromic acid, hydroiodic acid, nitric acid, pyrosulfuric acid and metaphosphoric acid or with an organic acid such as citric acid, benzoic acid, acetic acid, propionic acid, fumaric acid, maleic acid and sulfonic acid (for example, methanesulfonic acid, p-toluene sulfonic acid, naphthalene sulfonic acid).

Examples of a solvate of a compound represented by the formula (I) or (II), or a salt thereof include a hydrate.

A compound represented by the formula (I) can be produced, for example, according to the method described in Shi, D. Q. et al. J. Heterocyclic Chem. 2009, 46, 1331-1334, or Tu. S. et al. Bioorg. Med. Chem. Lett. 2006, 16, 3578-3581, as follows.

[Formula 8]

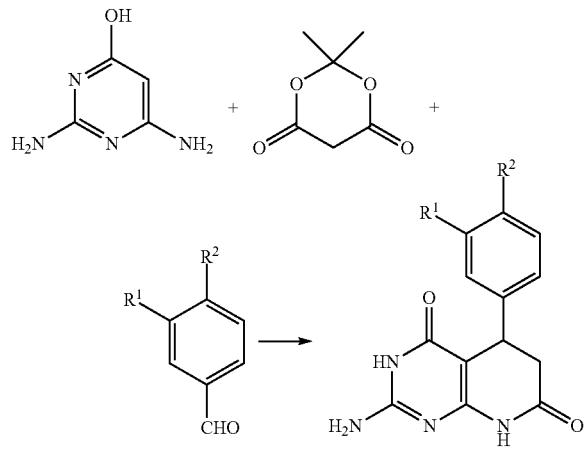

wherein $R^1$ and $R^2$ have the same meaning as defined in the formula (I).

Specifically, a target compound (I) can be manufactured by heating and reacting the corresponding aromatic aldehyde compound, 2,4-diamino-6-hydroxypyrimidine (another name: 2,6-diaminopyrimidin-4(3H)-one) and Meldrum's acid, (i) in water in the presence of triethylbenzylammonium chloride, (ii) while being irradiated with a microwave, or (iii) in an organic solvent.

A compound represented by the formula (II) can be produced, for example, according to the method described in JP Patent Publication (Kohyo) 2006-510596 A, as follows.

[Formula 9]

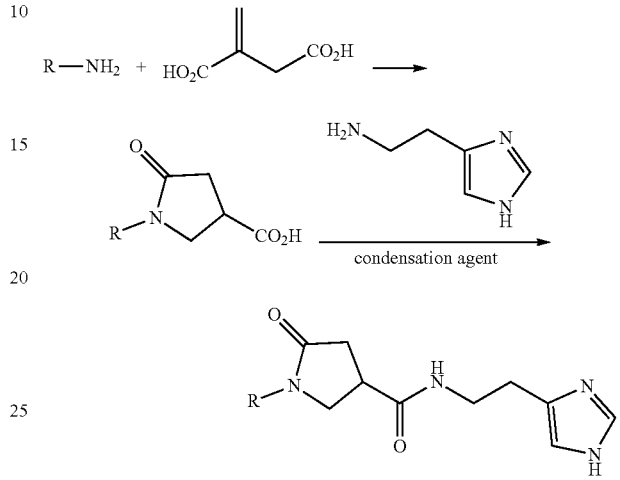

wherein R has the same meaning as defined in the formula (II).

Specifically, a target compound (II) can be manufactured by reacting the corresponding amine compound and itaconic acid to convert them into γ-lactam carboxylic acid, and then reacting the γ-lactam carboxylic acid with histamine in the presence of a condensing agent (for example, carbodiimide).

The product obtained as mentioned above may be purified by a customary method, for example, column chromatography using, e.g., silica gel, as a carrier and a recrystallization method using, e.g., methanol, ethanol, chloroform, dimethyl sulfoxide, n-hexane-ethyl acetate or water. Examples of an elution solvent for column chromatography include methanol, ethanol, chloroform, acetone, hexane, dichloromethane, ethyl acetate and mixed solvents of these.

The compound as mentioned above can be used as an analgesic drug in combination with a customary pharmaceutical carrier. The dosage form thereof is not particularly limited and appropriately selected and used depending on needs. Examples of the dosage form include oral agents such as a tablet, a capsule, a granule, a fine granule, a powder, a sustained release preparation, a liquid preparation, a suspension, an emulsion, a syrup and an elixir and parenteral agents such as an injection and a suppository.

An oral agent is produced by using, for example, starch, lactose, sucrose, mannitol, carboxymethylcellulose and inorganic salts in accordance with an ordinary method. In addition to these components, e.g., a binder, a disintegrant, a surfactant, a lubricant, a glidant, a flavoring agent, a colorant and/or a perfume can be appropriately added.

Examples of the binder include starch, dextrin, gum Arabic, gelatin, hydroxypropyl starch, methylcellulose, sodium carboxymethylcellulose, hydroxypropylcellulose, crystalline cellulose, ethylcellulose, polyvinyl pyrrolidone and macrogol.

Examples of the disintegrant include starch, hydroxypropyl starch, sodium carboxymethylcellulose, calcium carboxymethylcellulose, carboxymethylcellulose and a low-substituted hydroxypropylcellulose.

Examples of the surfactant include sodium lauryl sulfate, soy lecithin, sucrose fatty acid ester and polysorbate 80.

Examples of the lubricant include talc, wax, hydrogenated vegetable oil, sucrose fatty acid ester, magnesium stearate, calcium stearate, aluminum stearate and polyethylene glycol.

Examples of the glidant include light anhydrous silicic acid, dry aluminum hydroxide gel, synthetic aluminum silicate and magnesium silicate.

An injection is produced in accordance with an ordinary method. As a diluent, generally, distilled water for injection, saline, a glucose solution, olive oil, sesame oil, peanut oil, soybean oil, corn oil, propylene glycol, polyethylene glycol, and/or the like can be used. If necessary, a disinfectant, a preservative, a stabilizer, an isotonic agent, a soothing agent, and/or the like may be added. In view of stability, an injection can be added in, e.g., a vial, frozen and subjected to ordinary lyophilization to remove a water content. From the lyophilized injection, a liquid preparation can be prepared again immediately before use. The content of a compound of the formula (I) or (II) in the injection may be varied between the 5 and 50 wt %; however, the content is not limited to this.

Examples of other parenteral agents include a suppository for intrarectal administration. The suppository can be produced in accordance with an ordinary method.

The administration schedule of an analgesic drug formulated varies depending on, e.g., the dosage form and the route of administration, and, for example, can be administered once to four times per day in a period from a week to 3 months.

In order to obtain a desired effect, the dose of an oral agent, which varies depending on the age, body weight and severity of a disease of a patient, is usually, for example, 0.1 to 1000 mg and preferably 1 to 500 mg per adult in terms of the weight of a compound of the formula (I) or (II), and suitably divided into several portions per day and administered.

In order to obtain a desired effect, the dose of a parenteral agent, which varies depending on the age, body weight and severity of a disease of a patient, is usually, for example, 0.1 to 1000 mg and preferably 1 to 500 mg per adult in terms of the weight of a compound of the formula (I) or (II), and suitably administered by intravenous injection, intravenous drip infusion, subcutaneous injection or intramuscular injection.

The analgesic drug according to the present invention can be used for treating and/or preventing a disease or symptom selected from the group consisting of neuropathic pain (for example, peripheral neuropathic pain associated with external wound, and peripheral neuropathic pain associated with cancer chemotherapy), pain associated with cancer chemotherapy, diabetic neuralgia, diabetic peripheral neuropathic pain, and migraine.

This description includes part or all of the content as disclosed in the description and/or drawing of Japanese Patent Application No. 2017-186447, which is a priority document of the present application.

EXAMPLES

Now, the present invention will be more specifically described below by way of Examples; however, the scope of the present invention is not limited to them.

[Example 1] Synthesis of Pyrido[2,3-d]Pyrimidine Derivatives

[Formula 10]

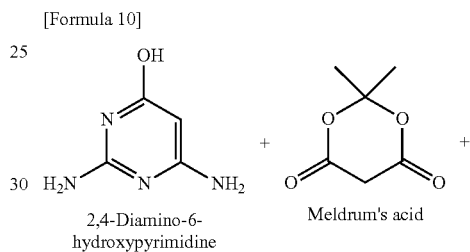

2,4-Diamino-6-hydroxypyrimidine      Meldrum's acid

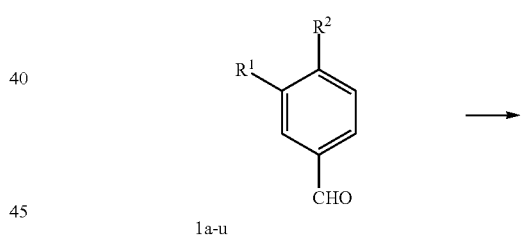

1a-u

1a: $R^1$ = Me, $R^2$ = OEt
1b: $R^1$ = OMe, $R^2$ = OEt
1c: $R^1$ = OMe, $R^2$ = On-Pr[2)]
1d: $R^1$ = $R^2$ = OEt
1e: $R^1$ = $R^2$ = F
1f: $R^1$ = Br, $R^2$ = OEt
1g: $R^1$ = OEt, $R^2$ = OMe
1h: $R^1$ = O(CH$_2$CH=CH$_2$), $R^2$ = OMe[3)]
1i: $R^1$ = On-Pr, $R^2$ = OMe[4)]
1j: $R^1$ = OEt, $R^2$ = H
1k: $R^1$ = O(CH$_2$CH=CH$_2$), $R^2$ = H
1l: $R^1$ = Cl, $R^2$ = OEt[5)]
1m: $R^1$ = Cl, $R^2$ = H
1n: $R^1$ = Br, $R^2$ = H
1o: $R^1$ = OCF$_3$, $R^2$ = H
1p: $R^1$ = OMe, $R^2$ = H
1q: $R^1$ = On-Pr, $R^2$ = H
1r: $R^1$ = Ph, $R^2$ = H
1s: $R^1$ = Et, $R^2$ = H[6)]
1t: $R^1$ = n-Pr, $R^2$ = H[7)]
1u: $R^1$ = n-Bu, $R^2$ = H

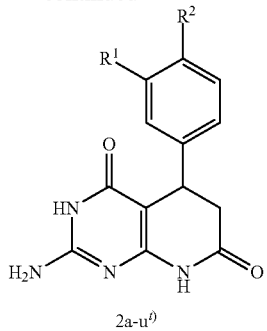

2a-u[i]

2a: R[1] = Me, R[2] = OEt (45%)
2b: R[1] = OMe, R[2] = OEt (37%)
2c: R[1] = OMe, R[2] = On-Pr (38%)
2d: R[1] = R[2] = OEt (41%)
2e: R[1] = R[2] = F (34%)
2f: R[1] = Br, R[2] = OEt (40%)
2g: R[1] = OEt, R[2] = OMe (45%)
2h: R[1] = O(CH$_2$CH=CH$_2$), R[2] = OMe (35%)
2i: R[1] = On-Pr, R[2] = OMe (41%)
2j: R[1] = OEt, R[2] = H (43%)
2k: R[1] = O(CH$_2$CH=CH$_2$), R[2] = H (45%)
2l: R[1] = Cl, R[2] = OEt (30%)
2m: R[1] = Cl, R[2] = H (35%)[3]
2n: R[1] = Br, R[2] = H (25%)
2o: R[1] = OCF$_3$, R[2] = H (23%)
2p: R[1] = OMe, R[2] = H (35%)
2q: R[1] = On-Pr, R[2] = H (32%)
2r: R[1] = Ph, R[2] = H (37%)
2s: R[1] = Et, R[2] = H (37%)
2t: R[1] = n-Pr, R[2] = H (18%)
2u: R[1] = n-Bu, R[2] = H (30%)

aldehydes (1a, b, d, e, f, g, j, k, m, n, o, p, q and r) and the aldehydes known in Literatures (1c, h, i, l, s and t) in ethylene glycol (0.5 mL) were sequentially added at room temperature 2,4-diamino-6-hydroxypyrimidine (0.67 mmol) and Meldrum's acid (1.00 mmol), and the mixture was stirred at 100° C. for 20 hours in an Ar atmosphere in accordance with a method described in Literature[1]. The reaction liquid was let to cool, then filtered, and further washed with methanol (0.5 mL×3) to obtain pale yellow crystals 2a to u, respectively.

2-Amino-5-(4-ethoxy-3-methylphenyl)-5,8-dihydro-3H,6H-pyrido[2,3-d]pyrimidine-4,7-dione (2a)

Yield: 46%; mp: >300° C.; IR (KBr): 3455, 3166, 2856, 2699, 1578, 1477 cm$^{-1}$; $^1$H NMR (400 MHz, DMSO-d6): δ 10.55 (1H, br s), 10.01 (1H, s), 6.90 (1H, d, J=2.4 Hz), 6.84 (1H, dd, J=8.8, 2.4 Hz), 6.77 (1H, d, J=8.8 Hz), 6.51 (2H, br s), 4.00 (1H, d, J=7.6 Hz), 3.95 (2H, q, J=7.0 Hz), 2.88 (1H, dd, J=16.0, 7.6 Hz), 2.42 (1H, d, J=16.0 Hz), 2.07 (3H, s), 1.29 (3H, t, J=7.0 Hz); $^{13}$C NMR (100 MHz, DMSO-d6): δ 171.10, 161.42, 156.45, 155.20, 154.95, 135.08, 128.74, 125.49, 124.61, 111.22, 92.07, 63.14, 32.12, 16.21, 14.83; MS (EI) m/z 314 (M+).

2-Amino-5-(4-ethoxy-3-methoxyphenyl)-5,8-dihydro-3H,6H-pyrido[2,3-d]pyrimidine-4,7-dione (2b)

Yield: 37%; mp: >300° C.; IR (KBr): 3462, 3309, 2850, 2743, 1582, 1521 cm$^{-1}$; $^1$H NMR (400 MHz, DMSO-d6): δ 10.57 (H, br s), 10.02 (1H, s), 6.84 (1H, d, J=2.3 Hz), 6.78 (1H, d, J=8.7 Hz), 6.53 (1H, dd, J=8.7, 2.3 Hz), 6.50 (2H, br s), 4.05 (1H, d, J=7.7 Hz), 3.92 (2H, q, J=6.9 Hz), 3.69 (3H, s), 2.88 (OH, dd, J=16.4, 7.7 Hz), 1.27 (3H, t, J=6.9 Hz); $^{13}$C NMR (100 MHz, DMSO-d6): δ 171.34, 161.47, 156.43, 155.01, 148.89, 146.63, 136.09, 117.65, 112.90, 111.24, 92.03, 63.73, 55.38, 38.71, 32.44, 14.81; MS (EI) m/z 330 (M+).

2-Amino-5-(3-methoxy-4-propoxyphenyl)-5,8-dihydro-3H,6H-pyrido[2,3-d]pyrimidine-4,7-dione (2c)

Yield: 38%; mp: >300° C.; IR (KBr): 3450, 3167, 2959, 2876, 1652, 1591 cm$^{-1}$; $^1$H NMR (400 MHz, DMSO-d6): δ 10.57 (1H, br s), 10.03 (1H, br s), 6.83 (1H, d, J=2.3 Hz), 6.79 (1H, d, J=8.4 Hz), 6.52 (1H, dd, J=8.4.2.3 Hz), 6.51 (2H, br s), 4.05 (1H, d, J=7.9 Hz), 3.82 (2H, t, J=7.1 Hz), 3.69 (3H, s), 2.88 (1H, dd, J=16.4, 7.9 Hz), 1.67 (2H, sext, J=7.1 Hz), 0.92 (3H, t, J=7.1 Hz); $^{13}$C NMR (100 MHz, DMSO-d6): δ 171.22, 161.69, 158.44, 157.50, 146.831, 145.48, 137.33, 117.79, 113.05, 111.44, 99.65, 69.86, 55.57, 38.73, 32.52, 22.20, 10.53; MS (EI) m/z 344 (M+).

2-Amino-5-(3,4-diethoxyphenyl)-5,8-dihydro-3H,6H-pyrido[2,3-d]pyrimidine-4,7-dione (2d)

Yield: 41%; mp: >300° C.; IR (KBr): 3188, 2977, 2868, 1653, 1635 cm$^{-1}$; $^1$H NMR (400 MHz, DMSO-d6): δ 10.57 (1H, s), 10.01 (1H, s), 6.81 (1H, d, J=1.8 Hz), 6.78 (1H, d, J=8.8 Hz), 6.53 (1H, dd, J=8.8, 1.8 Hz), 6.50 (2H, br s), 4.03 (1H, d, J=7.8 Hz), 3.93 (2H, q, J=6.9 Hz), 3.92 (2H, q, J=6.9 Hz), 2.87 (1H, dd, J=16.0, 7.8 Hz), 1.28 (3H, t, J=6.9 Hz), 1.26 (3H, t, J=6.9 Hz); $^{13}$C NMR (100 MHz, DMSO-d6): δ 171.27, 161.47, 156.42, 154.97, 148.11, 146.87, 136.19, 117.94, 113.45, 112.69, 92.07, 63.83, 63.78, 38.66, 32.37, 14.82; MS (EI) m/z 344 (M+).

2-Amino-5-(3,4-difluorophenyl)-5,8-dihydro-3H,6H-pyrido[2,3-d]pyrimidine-4,7-dione (2e)

Yield: 34%; mp: >300° C.; IR (KBr): 3471, 3161, 1646, 1592 cm$^{-1}$; $^1$H-NMR (400 MHz, DMSO-d6): δ 10.62 (1H, br s), 10.13 (1H, br s), 7.32 (1H, dt, J=10.8, 8.4 Hz), 7.18 (1H, ddd, J=10.8, 8.4, 2.4 Hz), 6.95 (1H, m), 6.57 (2H, brs), 4.12 (1H, d, J=7.2 Hz), 2.94 (1H, dd, J=16.3, 7.2 Hz) $^{13}$C NMR (125 MHz, DMSO-d6): δ 170.86, 161.41, 156.68, 155.24, 149.02, 147.17, 141.45, 122.88, 117.41 (d, J=17.0 Hz), 115.62 (d, J=17.0 Hz), 91.05, 38.22, 32.24; MS (EI) m/z 292 (M+).

2-Amino-5-(3-bromo-4-ethoxyphenyl)-5,8-dihydro-3H,6H-pyrido[2,3-d]pyrimidine-4,7-dione (2f)

Yield: 40%; mp: >300° C.; IR (KBr): 3458, 3080, 2863, 2751, 1540, 1475 cm$^{-1}$; $^1$H NMR (400 MHz, DMSO-d6): δ 10.57 (1H Kbr s), 10.09 (1H, s), 7.30 (H, d, J=2.4 Hz), 7.06 (1H, dd, J=8.0, 2.4 Hz), 6.99 (1H, d, J=8.0 Hz), 6.56 (2H, br s), 4.09 (1H, m), 4.04 (2H, q. J=7.1 Hz), 2.90 (1H, dd, J=16.2, 6.7 Hz), 1.31 (3H, t, J=7.1 Hz); $^{13}$C NMR (100 MHz, DMSO-d6): δ 170.93, 161.39, 156.55, 155.10, 153.29, 137.33, 130.87, 126.80, 113.77, 110.89, 91.53, 64.39, 38.47, 31.82, 14.58; MS (EI) m/z 379 (M+).

2-Amino-5-(3-ethoxy-4-methoxyphenyl)-5,8-dihydro-3H,6H-pyrido[2,3-d]pyrimidine-4,7-dione (2g)

Yield: 45%; mp: >300° C.; IR (KBr): 3461, 3160, 2841, 1591, 1516 cm$^{-1}$; $^1$H NMR (400 MHz, DMSO-d6): δ 10.58

(1H, br s), 10.03 (1H, s), 6.82 (1H, d, J=2.4 Hz), 6.80 (1H, d, J=8.4 Hz), 6.55 (1H, dd, J=8.4, 2.4 Hz), 6.50 (1H, brs), 4.04 (1H, d, J=7.8 Hz). 3.96-3.88 (2H, m), 3.68 (3H, s), 2.87 (1H, dd, J=16.0, 7.8 Hz), 1.28 (3H, t, J=7.2 Hz); $^{13}$C NMR (100 MHz, DMSO-d6): δ 171.30, 161.55, 156.51, 155.00, 147.88, 147.66, 136.10, 117.81, 112.20, 111.90, 92.11, 63.68, 55.54, 38.72, 32.42, 14.83; MS (EI) m/z 330 (M+).

5-(3-Allyloxy-4-methoxyphenyl)-2-amino-5,8-dihydro-3H,6H-pyrido[2,3-d]pyrimidine-4,7-dione (2h)

Yield: 35%; mp: >300° C.; IR (KBr): 3462, 3169, 1636, 1617, 1591 cm$^{-1}$; $^1$H NMR (400 MHz, DMSO-d6): δ 10.58 (1H, br s), 10.02 (1H, s), 6.84 (1H, d, J=2.0 Hz), 6.81 (1H, d, J=8.4 Hz), 6.57 (1H, dd, J=8.4, 2.0 Hz), 5.99 (1H, ddd, J=17.6, 10.4.5.2 Hz), 5.36 (1H, dd, J=17.6, 2.0 Hz), 5.22 (1H, dd, J=10.4.2.0 Hz), 4.46 (2H, d, J=5.2 Hz), 4.03 (1H, d, J=7.2 Hz), 3.68 (3H, s), 2.87 (11H, dd, J=15.8, 7.2 Hz); $^{13}$C NMR (100 MHz, DMSO-d6): δ 171.16, 158.72, 156.11, 154.99, 147.79, 147.55, 136.10, 133.95, 118.27, 117.88, 112.81, 112.09, 92.02, 69.10, 55.65, 32.41; MS (EI) m/z 342 (M+).

2-Amino-5-(4-methoxy-3-propoxyphenyl)-5,8-dihydro-3H,6H-pyrido[2,3-d]pyrimidine-4,7-dione (2i)

Yield: 41%; mp: >300° C.; IR (KBr): 3463, 3160, 2846, 1695, 1591, 1539, 1516 cm$^{-1}$; $^1$H NMR (400 MHz, DMSO-d6): δ 10.58 (H, br s), 10.03 (1H, s), 6.82 (1H, d, J=2.4 Hz), 6.80 (1H, dd, J=8.4, 2.4 Hz), 6.55 (1H, d, J=8.4 Hz), 6.51 (2H, br s), 4.04 (1H, d, J=7.2 Hz), 3.84-3.81 (2H, m), 3.67 (3H, s), 2.87 (1H, dd, J=16.4, 7.2 Hz), 1.68 (2H, sext, J=6.8 Hz), 0.94 (3H, t, J=6.8 Hz); $^{13}$C NMR (100 MHz, DMSO-d6): 171.24, 161.48, 156.43, 154.96, 148.04, 147.68, 136.14, 117.78, 112.27, 112.04, 92.06, 69.63, 55.61, 38.66, 32.38, 22.12, 10.46; MS (EI) m/z 344 (M+).

2-Amino-5-(3-ethoxyphenyl)-5,8-dihydro-3H,6H-pyrido[2,3-d]pyrimidine-4,7-dione (2j)

Yield: 43%; mp: >300° C.; IR (KBr): 3447, 3170, 2854, 1592, 1539 cm$^{-1}$; $^1$H NMR (400 MHz, DMSO-d6): δ 10.58 (1H, br s), 10.06 (1H, s), 7.15 (1H, t, J=7.8 Hz), 6.72 (I H, dd, J=7.8, 2.4 Hz), 6.70 (1H, dd, J=7.8, 2.4 Hz), 6.66 (1H, d, J=2.4 Hz), 6.53 (2H, brs), 4.07 (1H, d, J=7.4 Hz), 3.94 (2H, q, J=6.0 Hz), 2.91 (1H, dd, J=16.3, 7.4 Hz), 1.28 (3H, t, J=6.0 Hz); $^{13}$C NMR (100 MHz, DMSO-d6): δ 171.04, 161.40, 158.57, 156.59, 155.03, 145.32, 129.28, 118.56, 113.19, 111.58, 91.65, 62.78, 38.50, 32.86, 14.65; MS (EI) m/z 300 (M+).

5-(3-Allyloxyphenyl)-2-amino-5,8-dihydro-3H,6H-pyrido[2,3-d]pyrimidine-4,7-dione (2k)

Yield: 45%; mp: >300° C.; IR (KBr): 3085, 2855, 2727, 1520 cm$^{-1}$; $^1$H NMR (400 MHz, DMSO-d6): δ 10.58 (1H, br s), 10.06 (1H, s), 7.15 (1H, t, J=7.6 Hz), 6.76 (1H, dd, J=7.6, 2.4 Hz), 6.71 (2H, m), 6.53 (2H, br s), 6.00 (1H, ddd, J=17.4, 10.6, 5.5 Hz), 5.36 (1H, dd, J=17.4, 1.6 Hz), 5.23 (1H, dd, J=10.6, 1.6 Hz), 4.48 (2H, d, J=5.5 Hz), 4.07 (1H, d, J=7.5 Hz), 3.89 (1H, dd, J=16.2, 7.5 Hz); $^{13}$C NMR (100 MHz, DMSO-d6): δ 171.09, 161.41, 158.26, 156.58, 155.06, 145.35, 133.75, 129.48, 118.78, 117.56, 113.43, 112.03, 91.60, 68.11, 38.50, 32.86; MS (EI) m/z 312 (M+).

2-Amino-5-(3-chloro-4-ethoxyphenyl)-5,8-dihydro-3H,6H-pyrido[2,3-d]pyrimidine-4,7-dione (2l)

Yield: 30%; mp: >300° C.; IR (KBr): cm$^{-1}$; $^1$H NMR (400 MHz, DMSO-d6): δ 10.60 (1H, br s), 10.09 (1H, s), 7.15 (1H, s), 7.02 (2H, s), 6.55 (2H, brs), 4.06 (1H, d, J=8.0 Hz), 4.05 (2H, q, J=7.0 Hz), 2.91 (1H, dd, J=16.0, 8.0 Hz), 1.31 (3H, t, J=7.0 Hz); $^{13}$C NMR (100 MHz, DMSO-d6): δ 171.0, 161.38, 156.52, 155.11, 153.38, 136.81, 127.90, 126.09, 121.07, 113.90, 91.53, 64.28, 38.42, 31.87, 14.57.

2-Amino-5-(3-chlorophenyl)-5,8-dihydro-3H,6H-pyrido[2,3-d]pyrimidine-4,7-dione (2m)

Yield: 35%; mp: >300° C.; IR (KBr): cm$^{-1}$; $^1$H NMR (400 MHz, DMSO-d6): δ 10.61 (1H, br s), 10.11 (1H, s), 7.30 (1H, t, J=8.0 Hz), 7.24 (1H, d, J=8.0 Hz), 7.16 (1H, s), 7.11 (1H, d, J=8.0 Hz), 6.57 (2H, br s), 4.13 (1H, d, J=8.0 Hz), 2.95 (1H, dd, J=16.0, 8.0 Hz); $^{13}$C NMR (100 MHz, DMSO-d6): δ 170.85, 161.42, 156.76, 155.18, 146.35, 133.07, 130.46, 126.49, 126.41, 125.20, 91.61, 38.24, 32.72.

2-Amino-5-(3-bromophenyl)-5,8-dihydro-3H,6H-pyrido[2,3-d]pyrimidine-4,7-dione (2n)

Yield: 25%; mp: >300° C.; IR (KBr): cm$^{-1}$; $^1$H NMR (400 MHz, DMSO-d6): δ 10.61 (1H, br s), 10.12 (1H, s), 7.38 (1H, d, J=8.0, 1.8 Hz), 7.31 (1H, t, J=1.8 Hz), 7.24 (1H, t, J=8.0 Hz), 7.14 (1H, d, J=8.0 Hz), 6.57 (2H, brs), 4.12 (1H, d, J=8.0 Hz), 2.95 (1H, dd, J=16.2.8.0 Hz); $^{13}$C NMR (100 MHz, DMSO-d6): δ 170.81, 161.40, 156.74, 155.18, 146.63, 130.77, 129.38, 129.30, 125.57, 121.78, 91.03, 38.25, 32.71.

2-Amino-5-(3-trifluoromethoxyphenyl)-5,8-dihydro-3H,6H-pyrido[2,3-d]pyrimidine-4,7-dione (2o)

Yield: 23%; mp: >300° C.; IR (KBr): cm$^{-1}$; $^1$H NMR (400 MHz, DMSO-d6): δ 10.64 (1H, br s), 10.15 (1H, s), 7.40 (1H, t, J=8.0 Hz), 7.17 (2H, t, J=8.0 Hz), 7.12 (1 s), 6.58 (2H, brs), 4.18 (1H, d, J=7.2 Hz), 2.97 (1H, dd, J=16.2, 7.2 Hz); $^{13}$C NMR (100 MHz, DMSO-d6): δ 171.26, 161.71, 156.92, 155.40, 148.72, 146.70, 130.66, 120.22 (q, J=254.60 Hz), 119.21, 119.08, 116.41, 91.23, 38.31, 32.81.

2-Amino-5-(3-methoxyphenyl)-5,8-dihydro-3H,6H-pyrido[2,3-d]pyrimidine-4,7-dione (2p)

Yield: 35%; mp: >300° C.; IR (KBr): cm$^{-1}$; $^1$H NMR (400 MHz, DMSO-d6): δ 10.60 (1H, br s), 10.07 (1H, s), 7.17 (1H, t, J=7.6 Hz), 6.75 (1H, dd, J=7.6, 2.4 Hz), 6.71 (1H, d, J=2.4 Hz), 6.70 (1H, s), 6.54 (2H, br s), 4.08 (1H, d, J=7.2 Hz), 3.69 (3H, s), 2.92 (1H, dd, J=16.0, 7.2 Hz); $^{13}$C NMR (100 MHz, DMSO-d6): δ 171.24, 161.45, 159.34, 156.54, 155.11, 145.32, 129.53, 118.56, 112.85, 111.29, 91.65, 54.91, 38.51, 32.89.

2-Amino-5-(3-propoxyphenyl)-5,8-dihydro-3H,6H-pyrido[2,3-d]pyrimidine-4,7-dione (2q)

Yield: 32%; mp: >300° C.; IR (KBr): cm$^{-1}$; $^1$H NMR (400 MHz, DMSO-d6): δ 10.58 (1H, br s), 10.05 (1H, s), 7.15 (1H, t, J=8.0 Hz), 6.74-6.67 (3H, m), 6.52 (2H, br s), 4.07 (1H, d, J=8.0 Hz), 3.84 (2H, t, J=6.4 Hz), 2.91 (1H, dd, J=16.4, 8.0 Hz), 1.69 (2H, sext, J=6.4 Hz), 0.94 (3H, t, J=6.4 Hz); $^{13}$C NMR (100 MHz, DMSO-d6): δ 171.09, 161.47, 158.76, 156.62, 155.05, 145.34, 129.50, 118.54, 112.19, 111.74, 91.68, 68.76, 38.52, 32.89, 22.05, 10.47.

2-Amino-5-biphenyl-3-yl-5,8-dihydro-3H,6H-pyrido[2,3-d]pyrimidine-4,7-dione (2r)

Yield: 37%; mp: >300° C.; IR (KBr): cm$^{-1}$; $^1$H NMR (400 MHz, DMSO-d6): δ 10.58 (1H, br s), 10.09 (1H, s), 7.53 (2H, dd, J=8.0, 1.2 Hz), 7.42 (5H, m), 7.32 (2H, t, J=8.0 Hz), 7.01 (1H, d, J=8.0 Hz), 6.51 (2H, brs), 4.17 (1H, d, J=7.6 Hz), 2.95 (1H, dd, J=16.0, 7.6 Hz); $^{13}$C NMR (100 MHz, DMSO-d6): δ 171.38, 161.86, 155.22, 144.66, 140.62, 140.46, 129.37, 129.21, 127.71, 126.94, 126.85, 125.65, 125.20, 91.95, 62.93, 38.71, 33.17.

2-Amino-5-(3-ethylphenyl)-5,8-dihydro-3H,6H-pyrido[2,3-d]pyrimidine-4,7-dione (2s)

Yield: 37%; mp: >300° C.; IR (KBr): cm$^{-1}$; $^1$H NMR (400 MHz, DMSO-d6): δ 10.60 (1H, br s), 10.07 (1H, s), 7.15 (1H, t, J=8.0 Hz), 7.01 (1H, d, J=8.0 Hz), 7.00 (1H, s), 6.91 (1H, d, J=8.0 Hz), 6.53 (2H, brs), 4.08 (1H, d, J=7.2 Hz), 2.93 (1, dd, J=16.6, 7.2 Hz), 2.52 (2H, q, J=7.6 Hz), 1.13 (3H, t, J=7.6 Hz); $^{13}$C NMR (100 MHz, DMSO-d6): δ 171.27, 161.52, 156.60, 155.09, 143.76, 128.43, 126.14, 125.87, 123.66, 91.75, 62.82, 32.95, 28.24, 15.61.

2-Amino-5-(3-propylphenyl)-5,8-dihydro-3H,6H-pyrido[2,3-d]pyrimidine-4,7-dione (2t)

Yield: 18%; mp: >300° C.; IR (KBr): cm$^{-1}$; $^1$H NMR (400 MHz, DMSO-d6): δ 10.57 (1H, br s), 10.05 (1H, s), 7.14 (1H, t, J=7.6 Hz), 6.98 (1H, d, J=7.6 Hz), 6.97 (1H, s), 6.91 (1H, d, J=7.6 Hz), 6.52 (2H, br s), 4.07 (1 d, J=8.0 Hz), 2.92 (1H, dd, J=16.2, 8.0 Hz), 1.52 (2H, sext, J=7.2 Hz), 0.86 (3H, t, J=7.2 Hz); $^{13}$C NMR (100 MHz, DMSO-d6): δ 171.20, 161.48, 156.59, 155.04, 143.66, 142.24, 128.32, 126.63, 126.43, 123.73, 91.75, 38.87, 37.38, 32.90, 24.18, 13.74.

2-Amino-5-(3-butylphenyl)-5,8-dihydro-3H,6H-pyrido[2,3-d]pyrimidine-4,7-dione (2u)

Yield: 30%; mp: >300° C.; IR (KBr): cm$^{-1}$; $^1$H NMR (400 MHz, DMSO-d6): δ 10.57 (1H, br s), 10.01 (1H, s), 7.13 (1H, t, J=7.6 Hz), 6.98 (1H, d, J=7.6 Hz), 6.97 (1H, s), 6.90 (1H, d, J=7.6 Hz), 6.52 (2H, brs), 4.07 (1H, d, J=8.0 Hz), 2.92 (1H, dd, J=16.4, 8.0 Hz), 1.48 (2H, quin, J=7.4 Hz), 1.27 (2H, sext, J=7.4 Hz), 0.87 (3H, t, J=7.4 Hz); $^{13}$C NMR (100 MHz, DMSO-d6): δ 171.16, 161.46, 156.59, 155.04, 143.66, 142.42, 128.33, 126.59, 126.39, 123.67, 91.76, 38.70, 34.93, 33.20, 32.90, 21.82, 13.82.

1) Tu, S. et al. Bioorg. Med. Chem. Lett. 2006, 16, 3578-3581.
2) Muskinja. J. et al. Med. Chem. Res. 2016, 25, 1744-1753.
3) McDonald, B. et al. Org. Lett. 2015, 17, 98-101.
4) US 2015/0210682A
5) JP Patent Publication (Kohyo) 2010-526138 A
6) Wang, B. et al. Eur. J. Org. Chem. 2009, 22, 3688-3692.
7) WO 2008/136756
8) Shi, D. Q. et al. J. Heterocyclic Chem. 2009, 46, 1331-1334.

[Example 2] Synthesis of PA-9 Derivatives

[Formula 11]

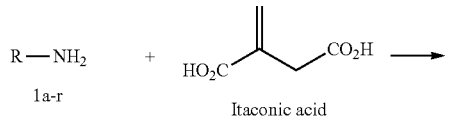

Itaconic acid

1a: R = 4-Cl-indazol[3)]
1b: R = 5-Cl-indazol[3)]
1c: R = 6-Cl-indazol[3)]
1d: R = 7-Cl-indazol[3)]
1e: R = Ph
1f: R = 4-Me-Ph
1g: R = 4-Cl-Ph
1h: R = 4-F-Ph
1i: R = 4-OMe-Ph
1j: R = 4-CN-Ph
1k: R = 2-OH-Ph
1l: R = 3-OH-Ph
1m: R = 4-OH-Ph
1n: R = pyrazol
1o: R = Bn
1p: R = 2-OH-Bn[4)]
1q: R = 3-OH-Bn[4)]
1r: R = 4-OH-Bn

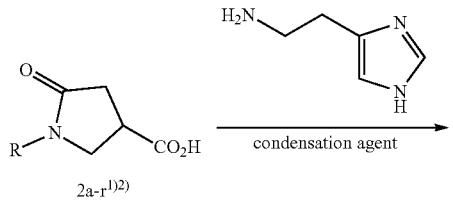

2a-r[1)2)]

2a: R = 4-Cl-indazol
2b: R = 5-Cl-indazol
2c: R = 6-Cl-indazol
2d: R = 7-Cl-indazol
2e: R = Ph
2f: R = 4-Me-Ph
2g: R = 4-Cl-Ph
2h: R = 4-F-Ph
2i: R = 4-OMe-Ph
2j: R = 4-CN-Ph
2k: R = 2-OH-Ph
2l: R = 3-OH-Ph
2m: R = 4-OH-Ph
2n: R = pyrazol
2o: R = Bn
2p: R = 2-OH-Bn
2q: R = 3-OH-Bn
2r: R = 4-OH-Bn

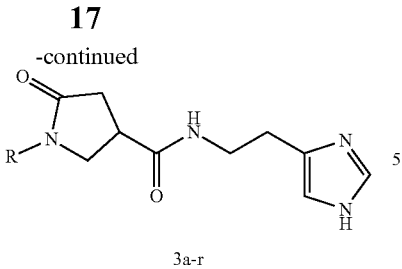

3a-r

3a: R = 4-Cl-indazol (—%)
3b: R = 5-Cl-indazol (24% over two steps)
3c: R = 6-Cl-indazol (17% over two steps)
3d: R = 7-Cl-indazol (36% over two steps)
3e: R = Ph (63%)
3f: R = 4-Me-Ph (93%)
3g: R = 4-Cl-Ph (93%) [5)]
3h: R = 4-F-Ph (94%)
3i: R = 4-OMe-Ph (95%)
3j: R = 4-CN-Ph (69%)
3k: R = 2-OH-Ph (40%)
3l: R = 3-OH-Ph (58%)
3m: R = 4-OH-Ph (54%)
3n: R = pyrazol (30%)
3o: R = Bn (76%) [8)]
3p: R = 2-OH-Bn (30%)
3q: R = 3-OH-Bn (40%)
3r: R = 4-OH-Bn (29%)

The corresponding amine from the amines 1a to d (1.0 eq) and itaconic acid (1.0 eq) were mixed at room temperature, and the mixture was heated gradually from 60° C. to 150° C. in an Ar atmosphere in accordance with Literature[1)] (JP Patent Publication (Kohyo) 2006-510596 A). The mixture was heated at 150° C. for 30 minutes and then cooled to room temperature to obtain carboxylic acids 2a to d, respectively, as pale yellow solids. To a solution of the corresponding carboxylic acid from the carboxylic acids 2a to d (1.0 eq) in DMF were sequentially added at room temperature dicyclohexylcarbodiimide (DCC) (1.2 eq), l-hydroxybenzotriazole (HOBt) (1.2 eq) and histamine (1.2 eq), and the mixture was stirred for 15 hours. A crude product was obtained by distilling off the solvent, and the crude product was purified by silica gel chromatography ($CH_2Cl_2$:MeOH=5:1) and further washed with EtOAc:MeOH=5:1 (0.5 mL×3) to obtain 3a to d, respectively, as white solids.

1-(4-chloro-1H-indazol-3-yl)-5-oxo-3-pyrrolidinecarboxylic acid (2a)

$^1$H NMR (400 MHz, Pyridine-d5): δ 10.74 (1H, br s), 7.73 (1H, d, J=2.1 Hz), 7.45 (1H, d, J=8.6 Hz), 7.15 (1H, dd, J=2.1.8.6 Hz), 4.65 (1H, dd, J=13.0, 7.6 Hz), 4.44 (1H, t, J=7.6 Hz), 3.40 (1H, quint. J=7.6 Hz), 2.77 (1H, dd, J=17.6, 7.6 Hz), 2.60 (1H, dd, J=17.6, 7.6 Hz).

1-(5-chloro-1H-indazol-3-yl)-5-oxo-3-pyrrolidinecarboxylic acid (2b)

$^1$H NMR (400 MHz, Pyridine-d5): δ 11.53 (1H, br s), 7.38 (1H, d, J=8.4 Hz), 7.14 (1H, dd, J=8.4, 7.2 Hz), 6.93 (1H, d, J=7.2 Hz), 4.67 (1H, dd, J=13.0, 7.5 Hz), 4.52 (1H, t, J=7.5 Hz), 3.39 (1H, quint, J=7.5 Hz), 2.76 (1H, dd, J=17.5, 7.5 Hz), 2.57 (1H, dd, J=17.5, 7.5 Hz).

1-(6-chloro-1H-indazol-3-yl)-5-oxo-3-pyrrolidinecarboxylic acid (2c)

$^1$H NMR (400 MHz, Pyridine-d5): δ 11.63 (1H, br s), 7.71 (1H, d, J=9.0 Hz), 7.48 (1H, d, J=1.7 Hz), 6.88 (1H, dd, J=9.0, 1.7 Hz), 4.65 (1H, dd, J=13.0, 7.7 Hz), 4.44 (1H, t, J=7.7 Hz), 3.40 (1H, quint, J=7.7 Hz), 2.68 (1H, dd, J=17.1, 7.7 Hz), 2.60 (1H, dd, J=17.1, 7.7 Hz).

1-(7-chloro-1H-indazol-3-yl)-5-oxo-3-pyrrolidinecarboxylic acid (2d)

$^1$H NMR (400 MHz, Pyridine-d5): δ 11.66 (1H, br s), 7.67 (1H, d, J=8.7 Hz), 7.30 (1H, d, J=7.3 Hz), 6.86 (1H, dd, J=8.7, 7.3 Hz), 4.71 (1H, dd, J=13.4, 7.4 Hz), 4.48 (1H, t, J=7.4 Hz), 3.42 (1H, quint, J=7.4 Hz), 2.78 (1H, dd, J=17.6, 7.4 Hz), 2.61 (1H, dd, J=17.6, 7.4 Hz).

N-[2-(1H-imidazol-4-yl)ethyl]-1-(4-chloro-1H-indazol-3-yl)-5-oxo-3-pyrrolidinecarboxamide (3a)

mp: 190-191° C.; IR (KBr): 3566, 3437, 3306, 1695, 1636, 1558, 1508 $cm^{-1}$; $^1$H NMR (400 MHz, Pyridine-d5): δ 9.00 (H, br s), 7.96 (1H, s), 7.61 (1H, d, J=7.4 Hz), 7.14 (1H, t, J=7.4 Hz), 7.15 (1H, s), 6.98 (1H, d, J=7.4 Hz), 4.72 (1H, t, J=9.1 Hz), 3.96-3.85 (3H, m), 3.26 (1H, dd, J=15.6, 9.1 Hz), 3.11 (2H, t, J=6.8 Hz), 2.78 (1H, dd, J=15.6, 9.1 Hz); $^{13}$C NMR (100 MHz, DMSO-d6): δ 169.56, 168.62, 147.59, 134.59, 131.61, 126.70, 123.80, 119.28, 116.97, 115.67, 107.11, 48.23, 36.47, 32.61, 26.57.

N-[2-(1H-imidazol-4-yl)ethyl]-1-(5-chloro-1H-indazol-3-yl)-5-oxo-3-pyrrolidinecarboxamide (3b)

Yield: 24% over two steps; mp: 208-209° C.; IR (KBr): 3735, 3649, 3097, 1684, 1653, 1558, 1508 $cm^{-1}$; $^1$H NMR (400 MHz, Pyridine-d5): δ 9.04 (1H, br s), 8.05 (1H, s), 7.69 (1H, d, J=9.6 Hz), 7.68 (1H, s), 7.27 (1H, d, J=9.6 Hz), 7.71 (1H, s), 5.09 (1H, dd, J=13.6, 8.4 Hz), 4.73 (1H, t, J=8.4 Hz), 3.94-3.86 (3H, m), 3.28 (1H, dd, J=14.8, 8.4 Hz), 3.11 (2H, t, J=6.6 Hz), 2.84 (1H, dd, J=14.8, 8.4 Hz); $^{13}$C NMR (100 MHz, DMSO-d6): δ 169.63, 168.21, 145.55, 134.50, 133.79, 131.92, 127.15, 123.19, 118.50, 118.39, 116.85, 108.13, 48.33, 38.747, 36.33, 32.92, 26.53.

N-[2-(1H-imidazol-4-yl)ethyl]-1-(6-chloro-1H-indazol-3-yl)-5-oxo-3-pyrrolidinecarboxamide (3c)

Yield: 17% over two steps: mp: 196-198° C.; IR (KBr): 3290, 3213, 3101, 1683, 1636, 1558, 1508 $cm^{-1}$; $^1$H NMR (400 MHz, Pyridine-d5): δ 9.12 (1H, br s), 8.30 (1H, s), 7.83 (1H, s), 7.66 (1H, d, J=9.2 Hz), 7.25 (1H, s), 6.96 (1H, d, J=9.2 Hz), 5.03 (1H, dd, J=13.0, 8.3 Hz), 4.71 (1H, t, J=8.3 Hz), 3.91-3.84 (3H, m), 3.27 (1H, dd, J=15.2, 8.3 Hz), 3.12 (2H, t, J=6.4 Hz), 2.87 (1H, dd, J=15.2, 8.3 Hz); $^{13}$C NMR (100 MHz, DMSO-d6): δ 169.79, 168.28, 147.25, 134.03, 132.74, 132.42, 131.35, 121.77, 119.93, 116.53, 115.03, 106.65, 48.23, 38.21, 36.25, 32.92, 25.47.

N-[2-(1H-imidazol-4-yl)ethyl]-1-(7-chloro-1H-indazol-3-yl)-5-oxo-3-pyrrolidinecarboxamide (3d)

Yield: 36% over two steps; mp: 238-239° C.; IR (KBr): 3319, 3231, 3213, 1663, 1636, 1558, 1508 $cm^1$; $^1$H NMR (400 MHz, Pyridine-d5): δ 9.02 (1H, br s), 8.49 (1H, s), 7.76 (1H, s), 7.52 (1H, d, J=7.5 Hz), 7.40 (1H, 1d, J=7.5 Hz), 6.98 (1H, s), 6.88 (1H, 1t, J=7.5 Hz), 5.13 (1H, dd, J=14.6, 8.5 Hz), 4.81 (1H, t, J=8.5 Hz), 3.95-3.86 (3H, m), 3.26 (1H, dd, J=16.2, 8.5 Hz), 3.11 (2H, t, J=6.8 Hz), 2.83 (1H, dd, J=16.2, 8.5 Hz); $^{13}$C NMR (100 MHz, DMSO-d6): δ 169.56, 168.32, 144.32, 134.51, 133.83, 133.30, 125.80, 120.48, 119.42, 119.04, 116.84, 109.42, 48.36, 38.77, 36.32, 32.95, 26.57.

To an aqueous solution of the corresponding amine from the amines 1e to j (1.0 eq) (3 mL) was added at room temperature itaconic acid (1.2 eq), and the mixture was heated and refluxed with stirring for 20 hours in an Ar atmosphere in accordance with Literature[2] (JP Patent Publication (Kohyo) No. 2012-529476 A). The mixture was cooled to room temperature, and a depositing solid was then filtered to obtain carboxylic acids 2e to j, respectively. To a solution of the corresponding carboxylic acid from the carboxylic acids 2e to j (1.0 eq) in a mixture of $CH_2Cl_2$ and DMF were sequentially added at room temperature 1-ethyl-3-(3-dimethylaminopropyl)carbodiimide (EDC) (1.2 eq), 4-dimethylaminopyridine (DMAP) (0.1 eq) and histamine (1.2 eq), and the mixture was stirred for 15 hours. A crude product was obtained by distilling off the solvent, and purified by silica gel chromatography ($CH_2Cl_2$:MeOH=10:1) to obtain 3e to j, respectively, as white solids.

N-[2-(1H-imidazol-4-yl)ethyl]-1-phenyl-5-oxo-3-pyrrolidinecarboxamide (3e)

Yield: 63%; mp: 149-151° C.; IR (KBr): 3675, 3306, 1678, 1643, 1558 $cm^{-1}$; $^1$H NMR (400 MHz, Pyridine-d5): δ 9.11 (1H, t, J=5.8 Hz), 7.90 (1H, s), 7.72 (2H, d, J=8.4 Hz), 7.28 (2H, t, J=8.4 Hz), 7.09 (1H, s), 7.06 (1H, t, J=8.4 Hz), 4.13 (1H, dd. J=9.6, 8.3 Hz), 3.93 (1H, t, J=8.3 Hz), 3.83 (2H, q, J=7.5 Hz), 3.47 (1H, quint, J=8.3 Hz), 3.14 (1H, dd, J=16.7, 8.3 Hz), 3.08 (2H, t, J=7.5 Hz), 2.84 (1H, dd, J=16.7, 8.3 Hz); $^{13}$C NMR (100 MHz, DMSO-d6): δ 172.16, 171.96, 139.22, 134.58, 133.95, 128.70, 124.00, 119.36, 116.83, 50.73, 38.66, 35.66, 35.43, 26.38.

N-[2-(1H-imidazol-4-yl)ethyl]-1-(4-methylphenyl)-5-oxo-3-pyrrolidinecarboxamide (3f)

Yield: 93%; mp: 176-178° C.; IR (KBr): 3306, 3088, 1675, 1639, 1556 $cm^{-1}$; $^1$H NMR (400 MHz, Pyridine-d5): δ 9.10 (H, t, J=5.8 Hz), 7.91 (1H, s), 7.64 (2H, d, J=7.2 Hz), 7.08 (2H, t, J=7.2 Hz), 7.07 (1H, s), 4.14 (1H, dd, J=9.6, 8.0 Hz), 3.92 (1H, t, J=8.0 Hz), 3.83 (2H, q, J=7.2 Hz), 3.46 (1H, quint, J=8.0 Hz), 3.14 (1H, dd, J=17.6, 8.0 Hz), 3.08 (2H, t, J=7.2 Hz), 2.84 (1H, dd, J=17.6, 8.0 Hz), 2.13 (3H, s); $^{13}$C NMR (100 MHz, DMSO-d6): δ 172.17, 172.10, 137.00, 134.86, 134.44, 133.26, 129.30, 119.58, 117.04, 51.00, 39.17, 36.02, 35.84, 27.01, 20.63.

1-(4-chlorophenyl)-N-[2-(1H-imidazol-4yl)ethyl]-5-oxo-3-pyrrolidinecarboxamide (3g)

Yield: 93%; mp: 196-198° C.; IR (KBr): 3119, 3017, 1695, 1647, 1558 $cm^{-1}$; $^1$H NMR (400 MHz, Pyridine-d5): δ 9.16 (H, t, J=5.2 Hz), 7.95 (1H, s), 7.71 (2H, d, J=8.4 Hz), 7.30 (2H, d, J=8.4 Hz), 7.11 (1H, s), 4.10 (1H, dd, J=9.4.8.3 Hz), 3.92 (1H, t, J=8.3 Hz), 3.83 (2H, q, J=6.7 Hz), 3.50 (1H, quint, J=8.3 Hz), 3.11 (1H, dd, J=17.5, 8.3 Hz), 3.09 (2H, t, J=5.7 Hz), 2.85 (1H, dd. J=17.5, 8.3 Hz); $^{13}$C NMR (100 MHz, DMSO-d6): δ 172.20, 171.68, 137.90, 134.43, 133.95, 128.36, 127.49, 120.60, 116.62, 50.47, 38.74, 35.62, 35.30, 26.52.

N-[2-(1H-imidazol-4-yl)ethyl]-1-(4-fluorophenyl)-5-oxo-3-pyrrolidinecarboxamide (3h)

Yield: 94%; mp: 232-234° C.; IR (KBr): 3140, 3126, 1688, 1645, 1570 $cm^{-1}$; $^1$H NMR (400 MHz, Pyridine-d5): δ 9.13 (1H, t, J=4.8 Hz), 7.72-7.68 (2H, m), 7.92 (1H, s), 7.11 (1H, s), 7.09-7.04 (2H, m), 4.12 (1H, dd, J=12.2, 8.7 Hz), 3.92 (1H, t, J=8.7 Hz), 3.84 (2H, t, J=7.0 Hz), 3.49 (1H, quint, J=8.7 Hz), 3.14 (1H, dd, J=17.2, 8.7 Hz), 3.09 (2H, t, J=7.0 Hz), 2.85 (1H, dd, J=17.2, 8.7 Hz); $^{13}$C NMR (100 MHz, DMSO-d6): δ 172.05, 171.90, 158.44 (d, J=240.3 Hz), 135.64, 134.62, 134.14, 121.35 (d, J=7.6 Hz), 116.81, 115.25 (d, J=22.0 Hz), 50.92, 38.92, 35.68, 35.58, 26.72.

N-[2-(1H-imidazol-4-yl)ethyl]-1-(4-methoxyphenyl)-5-oxo-3pyrrolidinecarboxamide (3i)

Yield: 95%; mp: 151-153° C.; IR (KBr): 3239, 3075, 1684, 1635, 1568 $cm^{-1}$; $^1$H NMR (400 MHz, Pyridine-d5): δ 9.08 (1H, t, J=5.2 Hz), 7.91 (1H, s), 7.68 (2H, d, J=8.6 Hz), 7.10 (1H, s), 6.92 (2H, d, J=8.6 Hz), 4.16 (1H, dd, J=9.4, 8.4 Hz), 3.93 (1H, t, J=8.4 Hz), 3.84 (2H, q, J=7.6 Hz), 3.62 (3H, s), 3.46 (1H, quint, J=8.4 Hz), 3.15 (1H, dd, J=17.1, 8.4 Hz), 3.09 (2H, t, J=7.6 Hz), 2.84 (1H, dd, J=17.1, 8.4 Hz); $^{13}$C NMR (100 MHz, DMSO-d6): δ 171.97, 171.57, 155.80, 134.65, 134.26, 132.41, 121.20, 116.80, 113.82, 55.20, 51.03, 38.95, 35.68, 35.62, 26.81.

N-[2-(1H-imidazol-4-yl)ethyl]-1-(4-cyanophenyl)-5-oxo-3-pyrrolidinecarboxamide (3j)

Yield: 69%; mp: 211-212° C.; IR (KBr): 3151, 3019, 2231, 1703, 1646, 1558 $cm^{-1}$; $^1$H NMR (400 MHz, Pyridine-d5): δ 9.17 (1H, t, J=5.2 Hz), 7.92 (1H, s), 7.83 (2H, d, J=8.8 Hz), 7.60 (2H, d, J=8.8 Hz), 7.11 (1H, s), 4.12 (H, dd, J=9.6, 8.4 Hz), 3.96 (1H, t, J=8.4 Hz), 3.84 (2H, t, J=7.0 Hz), 3.51 (1H, quint, J=8.4 Hz), 3.16 (1H, dd, J=17.2, 8.4 Hz), 3.10 (2H, t, J=7.0 Hz), 2.88 (H, dd, J=17.2, 8.4 Hz)$^{13}$C NMR (100 MHz, DMSO-d6): δ 173.28, 171.75, 143.03, 134.67, 133.06, 119.03, 118.93, 105.53, 51.51, 38.98, 36.03, 35.39, 26.85.

The corresponding amine from the amines k to m (1.0 eq) and itaconic acid (1.0 eq) were mixed at room temperature, and the mixture was heated gradually from 60° C. to 150° C. in an Ar atmosphere in accordance with Literature[1] (JP Patent Publication (Kohyo) 2006-510596 A). The mixture was heated at 150° C. for 30 minutes and then cooled to room temperature to obtain carboxylic acids 2k to m, respectively. To a solution of the corresponding carboxylic acid from the carboxylic acids 2k to m (1 eq) in a mixture of $CH_2Cl_2$ and DMF were sequentially added at room temperature EDC (1.2 eq), DMAP (0.1 eq) and histamine (1.2 eq), and the mixture was stirred for 15 hours. A crude product was obtained by distilling off the solvent, and purified by silica gel chromatography ($CH_2Cl_2$:MeOH=10:1) to obtain 3k to m as white, yellow and red foamy solids, respectively.

N-[2-(1H-imidazol-4-yl)ethyl]-1-(2-hydroxyphenyl)-5-oxo-3-pyrrolidinecarboxamide (3k)

Yield: 40%; IR (KBr): 3651, 3265, 3213, 1684, 1670, 1558 $cm^{-1}$; $^1$H NMR (400 MHz, Pyridine-d5): δ 9.08 (1H, br s), 7.91 (1H, s), 7.42 (1H, d, J=8.8 Hz), 7.21-7.15 (2H, m), 7.10 (1H, s), 6.92-6.88 (1H, m), 4.30 (1H, dd, J=9.2, 7.5 Hz), 4.10 (1H, t, J=7.5 Hz), 3.85 (2H, q, J=6.4 Hz), 3.47 (1H, quint, J=7.5 Hz), 3.13 (1H, dd, J=16.4, 7.5 Hz), 3.06 (2H, t, J=6.4 Hz), 2.83 (1H, dd, J=16.4, 7.5 Hz); $^{13}$C NMR (100 MHz, DMSO-d6): δ 172.52, 172.22, 152.77, 134.68, 128.30, 128.24, 125.48, 119.12, 118.74, 116.87, 116.74, 51.68, 38.98, 37.09, 34.39, 26.85.

N-[2-(1H-imidazol-4-yl)ethyl]-1-(3-hydroxyphenyl)-5-oxo-3-pyrrolidinecarboxamide (3l)

Yield: 58%; IR (KBr): 3790, 3439, 3337, 1684, 1653, 1558 cm$^{-1}$; $^1$H NMR (400 MHz, Pyridine-d5): δ 8.97 (1H, br s), 8.09 (1H, s), 7.93 (1H, s), 7.28 (1H, t, J=8.2 Hz), 7.20 (1H, d, J=8.2 Hz), 7.13 (1H, s), 6.98 (1H, d, J=8.2 Hz), 4.29 (1H, dd, J=9.0, 8.3 Hz), 3.98 (1H, t, J=8.3 Hz), 3.89 (1H, q, J=6.9 Hz), 3.36 (1H, quint, J=8.3 Hz), 3.21 (1H, dd, J=17.1, 8.3 Hz), 3.09 (2H, t, J=6.9 Hz), 2.82 (1H, dd, J=17.1, 8.3 Hz); $^{13}$C NMR (100 MHz, DMSO-d6): δ 172.07, 171.93, 157.55, 140.28, 134.68, 129.38, 111.17, 109.78, 106.63, 50.84, 39.00, 35.99, 35.54, 26.89.

N-[2-(1H-imidazol-4-yl)ethyl]-1-(4-hydroxyphenyl)-5-oxo-3-pyrrolidinecarboxamide (3m)

Yield: 54%; IR (KBr): 3585, 3251, 3190, 1684, 1653, 1558 cm$^{-1}$; $^1$H NMR (400 MHz, Pyridine-d5): δ 11.49 (1H, br s), 8.97 (1H, br s), 7.93 (1 s), 7.76 (2H, dd, J=8.6, 2.4 Hz), 7.15 (2H, dd, J=8.6, 2.4 Hz), 7.14 (1H, s), 4.29 (1H, td, J=8.4, 2.1 Hz), 3.95 (1H, td, J=8.4, 2.1 Hz), 3.90 (2H, q, J=6.3 Hz), 3.39 (1H, quint, J=8.4 Hz), 3.22 (1H, ddd, J=16.7, 8.4, 2.1 Hz), 3.10 (2H, t, J=6.3 Hz), 2.84 (1H, ddd, J=16.7, 8.4, 2.1 Hz); $^{13}$C NMR (100 MHz, DMSO-d6): δ 172.52, 171.86, 154.61, 135.20, 131.48, 122.05, 115.61, 51.67, 39.49, 36.23, 36.09, 27.40.

An amine in (1.0 eq) and itaconic acid (1.0 eq) were mixed at room temperature, and the mixture was heated gradually from 60° C. to 150° C. in an Ar atmosphere in accordance with Literature[1)] (JP Patent Publication (Kohyo) 2006-510596 A). The mixture was heated at 150° C. for 30 minutes and then cooled to room temperature to obtain a carboxylic acid 2n. To a solution of the carboxylic acid 2n (1.0 eq) in a mixture of CH$_2$Cl$_2$ and DMF were sequentially added at room temperature DCC (1.2 eq), HOBt (1.2 eq) and histamine (1.2 eq), and the mixture was stirred for 15 hours. A crude product was obtained by distilling off, and purified by silica gel chromatography (CH$_2$Cl$_2$:MeOH=10:1) to obtain 3n as a white solid.

N-[2-(1H-imidazol-4-yl)ethyl]-1-(1H-pyrazol-3-yl)-5-oxo-3-pyrrolidinecarboxamide (3n)

Yield: 30%; mp: 213-211° C.; IR (KBr): 3676, 3320, 3203, 1689, 1652, 1635, 1557 cm$^{-1}$; $^1$H NMR (400 MHz, Pyridine-d5): δ 12.24 (1H, br s), 9.00 (1H, br s), 8.03 (1H, s), 7.88 (1H, s), 7.56 (1H, s), 7.10 (1H, s), 4.78 (1H, dd, J=12.6, 8.1 Hz), 4.26 (1H, t, J=8.1 Hz), 3.82 (2H, q, J=6.7 Hz), 3.69 (1H, quint, J=8.1 Hz), 3.22 (1H, dd. J=15.3, 8.1 Hz), 3.06 (2H, t, J=6.7 Hz), 2.72 (1H, dd, J=15.3, 8.1 Hz); $^{13}$C NMR (100 MHz, DMSO-d6): δ 169.67, 168.26, 162.33, 138.77, 138.73, 134.64, 134.53, 89.01, 47.04, 38.87, 36.72, 33.00, 26.97.

The corresponding amine from the amines 1o to r (1.0 eq) and itaconic acid (1.0 eq) were mixed at room temperature, and the mixture was heated gradually from 60° C. to 150° C. in an Ar atmosphere in accordance with Literature[1] (JP Patent Publication (Kohyo) 2006-510596 A). The mixture was heated at 150° C. for 30 minutes, then cooled to room temperature and purified by silica gel chromatography (CH$_2$Cl$_2$:MeOH=30:1) to obtain carboxylic acids 2o to r, respectively. To a solution of the corresponding carboxylic acid from the carboxylic acids 2o to r (1.0 eq) in a mixture of CH$_2$Cl$_2$ and DMF were sequentially added at room temperature DCC (1.2 eq), HOBt (1.2 eq) and histamine (1.2 eq), and the mixture was stirred for 15 hours. A crude product was obtained by distilling off the solvent, and purified by silica gel chromatography (CH$_2$Cl$_2$:MeOH=10:1) to obtain 3o to r, respectively, as a yellow solid or a white foamy solid.

N-[2-(1H-imidazol-4yl)ethyl]-5-oxo-1-(phenylmethyl)-3-pyrrolidinecarboxamide (3o)

Yield: 29%; IR (KBr): 3271, 3155, 1670, 1652, 1558 cm$^{-1}$; H NMR (400 MHz, Pyridine-d5): δ 8.85 (1H, br), 7.92 (1H, s), 7.33-7.25 (5H, m), 7.08 (1H, s), 4.56 (H, d, J=14.6 Hz), 4.48 (1H, d, J=14.6 Hz), 3.85 (2H, q, J=6.5 Hz), 3.67 (1H, t, J=8.0 Hz), 3.39 (1H, t, J=8.0 Hz), 3.25 (1H, quint, J=8.0 Hz), 3.10 (11H, dd, J=17.0, 8.0 Hz), 3.05 (2H, t, J=6.5 Hz), 2.72 (1H, dd, J=17.0, 8.0 Hz).

N-[2-(1H-imidazol-4-yl)ethyl]-1-[(2-hydroxyphenyl)methyl]-5-oxo-3-pyrrolidinecarboxamide (3p)

Yield: 30%; IR (KBr): 3748, 3738, 3651, 1684, 1653, 1558 cm$^{-1}$; $^1$H NMR (400 MHz, Pyridine-d5): δ 11.36 (1H, br s) 8.81 (1H, t, J=5.8 Hz), 7.84 (1H, d, J=1.2 Hz), 7.34 (1H, dd, J=7.5, 1.3 Hz), 7.13 (1H, td, J=7.5, 1.3 Hz), 7.08 (1H, dd, J=7.5, 1.3 Hz), 7.03 (1H, s), 6.81 (1H, td, J=1.3, 7.5 Hz), 4.74 (1H, d, J=15.2 Hz), 4.65 (1H, d, J=15.2 Hz), 3.82 (1H, dd, J=9.6, 8.2 Hz), 3.77 (2H, q, J=6.6 Hz), 3.57 (1H, t, J=8.2 Hz), 3.22 (1H, quint, J=8.2 Hz), 3.03 (1H, dd, J=16.5, 8.2 Hz), 2.99 (2H, t, J=6.6 Hz), 2.63 (1H, dd, J=16.5, 8.2 Hz); $^{13}$C NMR (100 MHz, DMSO-d6): δ 172.57, 172.18, 155.26, 134, 67, 128.78, 128.38, 122.58, 119.03, 115.21, 49.63, 40.57, 38.94, 35.93, 33.91, 26.87.

N-[2-(1H-imidazol-4-yl)ethyl]-1-[(3-hydroxyphenyl)methyl]-5-oxo-3-pyrrolidinecarboxamide (3q)

Yield: 40%; IR (KBr): 3734, 3647, 3623, 1684, 1653, 1558 cm$^{-1}$; $^1$H NMR (40 MHz, Pyridine-d5): δ 8.83 (1H, br s), 7.93 (1H, s), 7.24 (2H, d, J=7.9 Hz), 7.22 (1H, s), 7.09 (1H, s), 7.08 (1H, d, J=7.9 Hz), 6.88 (1H, d, J=7.9 Hz), 4.57 (1H, d, J=14.6 Hz), 4.48 (1H, d, J=14.6 Hz), 3.84 (2H, q, J=6.1 Hz), 3.72 (1H, t, J=8.1 Hz), 3.45 (11H, t, J=8.1 Hz), 3.23 (1H, quint, J=8.1 Hz), 3.09 (1H, dd, J=16.0, 8.1 Hz), 3.05 (2H, t, J=6.1 Hz), 2.67 (1H, dd, J=16.0, 8.1 Hz); $^{13}$C NMR (100 MHz, DMSO-d6): δ 172.31, 172.05, 157.63, 138.14, 134.66, 134.18, 129.55, 118.17, 116.90, 114.41, 114.30, 49.14, 45.31, 38.88, 35.89, 26.78.

N-[2-(1H-imidazol-4-yl)ethyl]-1-[(4-hydroxyphenyl)methyl]-5-oxo-3-pyrrolidinecarboxamide (3r)

Yield: 29%; IR (KBr): 3651, 3271, 3213, 1663, 1653, 1558 cm$^{-1}$; $^1$H NMR (400 MHz, Pyridine-d5): δ 8.85 (1H, br s), 7.91 (1H, s), 7.28 (2H, d, J=7.6 Hz), 7.10 (2H, d, J=7.6 Hz), 4.55 (1H, d, J=14.6 Hz), 4.44 (1H, d, J=14.6 Hz), 3.91-3.71 (2H, m), 3.70 (1H, dd, J=8.8, 7.9 Hz), 3.45 (1H, t, J=7.9 Hz), 3.26 (1H, quint, J=7.9 Hz), 3.11 (1H, dd. J=15.0, 7.9 Hz), 3.06 (2H, t, J=7.4 Hz), 2.71 (1H, dd, J=15.0, 7.9 Hz); $^{13}$C NMR (100 MHz, DMSO-d5): δ 172.15, 156.66, 134.68, 129.07, 126.80, 115.30, 48.93, 44.83, 38.94, 35.83, 34.03, 26.89.

1) JP Patent Publication (Kohyo) 2006-510596 A
2) JP Patent Publication (Kohyo) 2012-529476 A
3) Saczewski, F. et al. Bioorg. Med. Chem. 2011, 19, 321-329
4) Mestichelli, P. et al. Org. Lett. 2013, 15, 5448-5451
5) Commercially available, Aurora Building Blocks, A17.818.885

6) Commercially available, Aurora Building Blocks, A21.884.126

[Example 3] Drug Efficacy Evaluation Using PACAP Receptor-Expressing. Cultured Cells The effect of each compound on the phosphorylation of CREB (cAMP-responsive element-binding protein) produced by a PACAP stimulus was examined by Western blot analysis using an anti-phosphorylated CREB (pCREB) antibody with a mouse PAC receptor-expressing CHO cell (PAC1/CHO cell) and a mouse VPAC1 receptor-expressing CHO cell (VPAC1/CHO cell).

Specifically, treatment with a compound (PA-8, PA-9, compounds 2j, 2o and 3d) at 10 μM to 10 nM or a solvent therefor (VEH: 0.1% DMSO-containing phosphate buffer solution) was performed for 30 minutes, 1 nM PACAP was then added, and protein was recovered within 30 minutes after a PACAP stimulus.

FIG. 1A shows data in the PAC/CHO cell, and PA-8 suppressed CREB phosphorylation by PACAP (1 nM) at the concentration at which PA-8 was used (10 μM to 10 nM) (n=5; FIG. 1A). Meanwhile, in the examination using the VPAC1/CHO cell, PA-8 did not suppress CREB phosphorylation by PACAP (1 nM) at the concentration at which PA-8 was used (10 μM to 10 nM) (n=3; FIG. 1B). That is, it can be said that PA-8 is a PAC1 receptor selective antagonistic drug.

Figure 2:
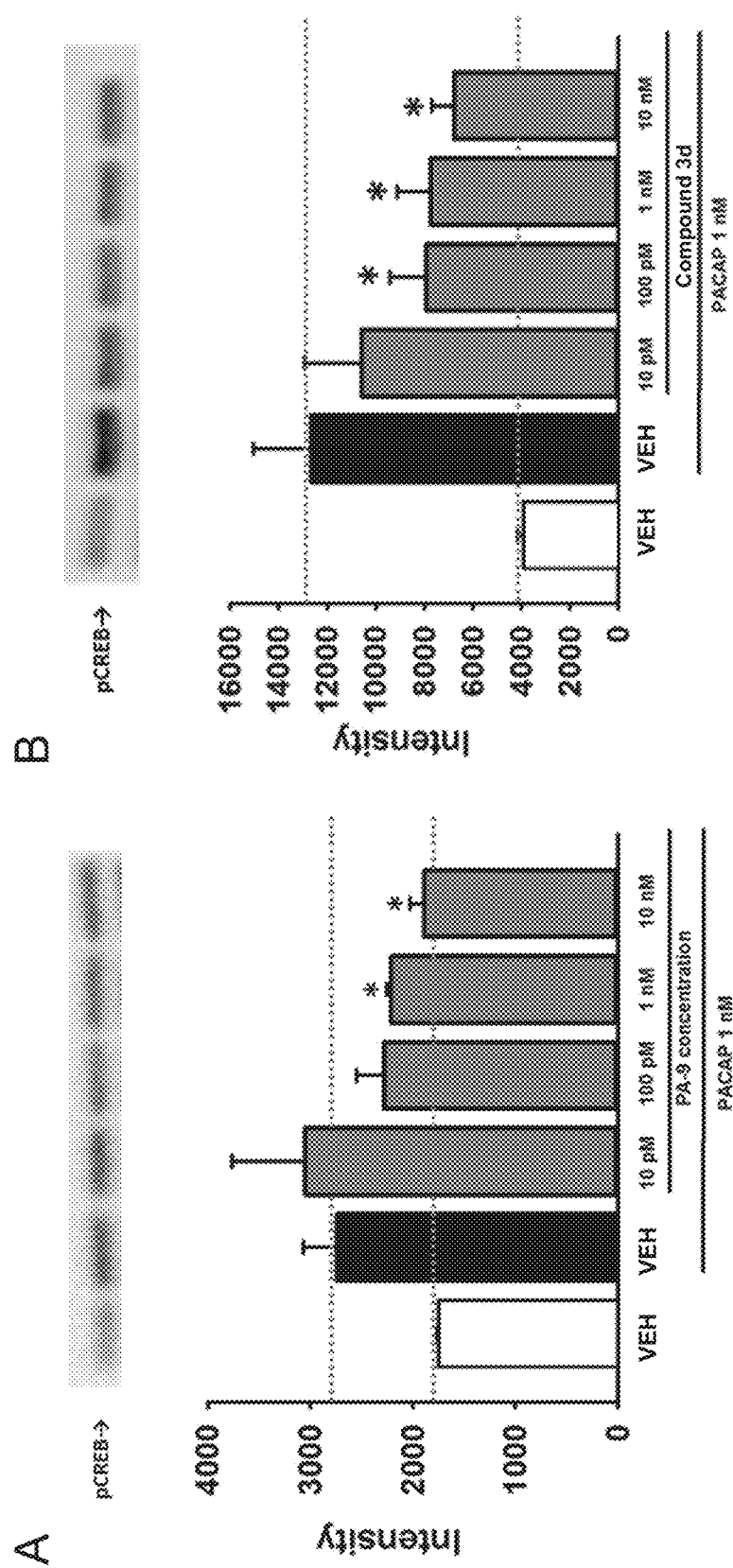
FIG. 2 shows the evaluation of PA-9 and a derivative thereof (compound 3d) using PACAP receptor-expressing cells.
Figure 3:
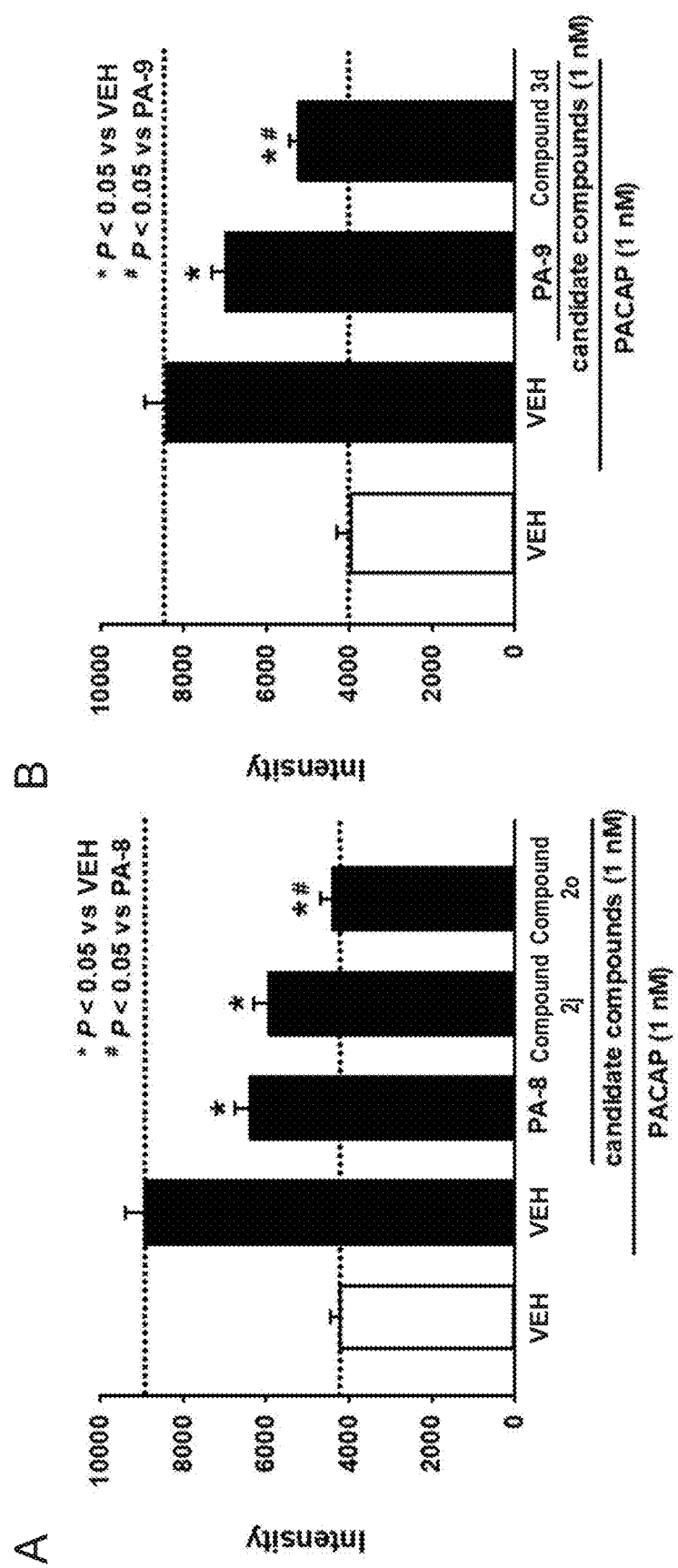
FIG. 3 shows the evaluation of PA-8, PA-9 and derivatives thereof (compounds 2j, 2o and 3d) using PACAP receptor-expressing cells.

FIG. 1C shows the effects of the compound 2j (10 μM to 10 nM) in the PAC1/CHO cell, and CREB phosphorylation by PACAP (1 nM) was suppressed depending on the concentration (n=4). FIG. 1D shows the effects of the compound 2o (10 μM to 10 nM) similarly. The compound 2o also suppressed CREB phosphorylation by PACAP (1 nM) at the concentration at which the compound 2o was used (10 μM to 10 nM) (n=4). FIGS. 2A and 2B shows the effects of PA-9 and the compound 3d (10 μM to 10 nM) in the PAC1/CHO cell, respectively, and both suppressed CREB phosphorylation by PACAP (1 nM) depending on the concentration (n=4 to 5). Especially the compound 2o and the compound 3d exhibited the significantly stronger effect of suppressing CREB phosphorylation at 1 nM than PA-8 and PA-9, respectively (n=4 to 5, FIG. 3).

As PA-8 and PA-9 used in the experiments, commercial compounds purchased from NAMIKI SHOJI CO., LTD. were used.

[Example 4] Drug Efficacy Evaluation 1 Using Mouse Pain Model (Spontaneous Pain-Like Behavior Induced by PACAP Intrathecal Administration)

When PACAP (100 pmol/5 L) is intrathecally administered to a mouse in a single dose (single i.t. injection), spontaneous pain-like behavior in which the mouse licks or bites the rear half of the body occurs about 5 minutes after the administration (and continues for several hours) (Ohnou et al. J. Pharmacol. Sci. 130, 194-203, 2016).

Figure 4:
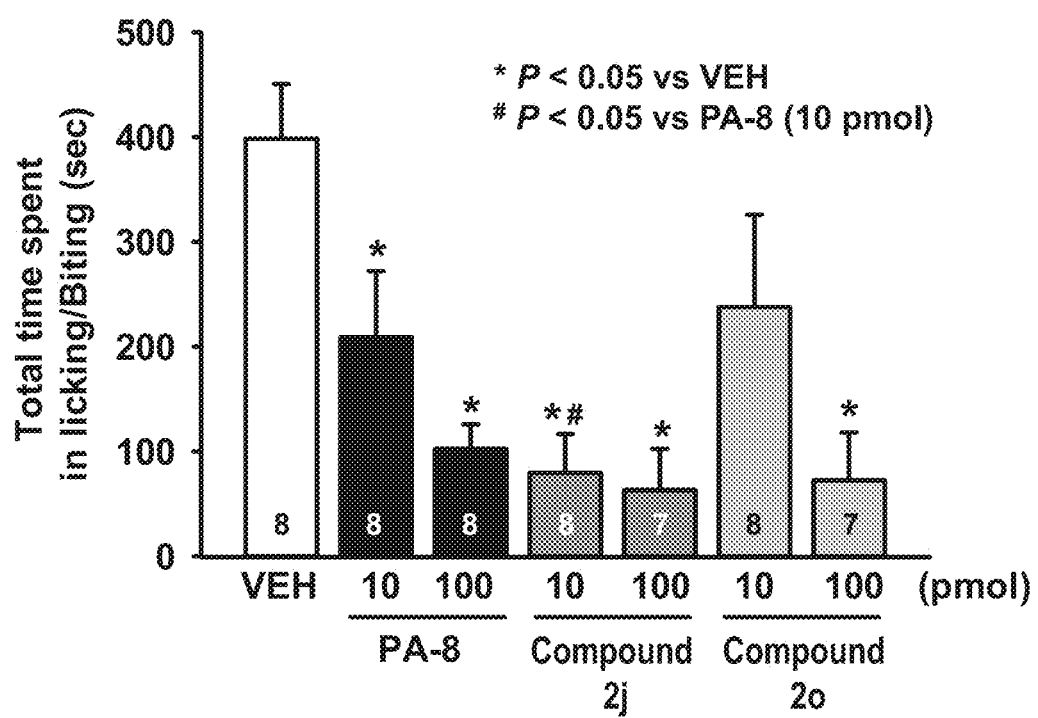
FIG. 4 shows the evaluation of drug efficacies (the effects of suppressing spontaneous pain-like behavior induced by PACAP intrathecal administration) using mouse pain models.

When simultaneous i.t. administration of PACAP (100 pmol) and PA-8, the compound 2j or the compound 2o (10 to 100 pmol/5 μL) was performed, all except the compound 2o (10 pmol) suppressed the PACAP response significantly, and the effect of the compound 2j (10 pmol) was significantly stronger than that of PA-8 (10 pmol), and was an effect equivalent or superior to that of PA-8 (100 pmol). Meanwhile, although the compound 2o did not exhibit a significant suppressing effect at 10 pmol, the compound 2o exhibited a suppressing effect equivalent to PA-8 and the compound 2j at 100 pmol (n=7 to 8, FIG. 4).

Male ddY mice (6 to 12 weeks old) were used, and the behaviors were taken on video. The number of times of spontaneous pain-like behaviors for 30 minutes after the administration was counted.

[Example 5] Drug Efficacy Evaluation 2 Using Mouse Pain Model (Mechanical Allodynia Induced by PACAP Intrathecal Administration)

Figure 5A:
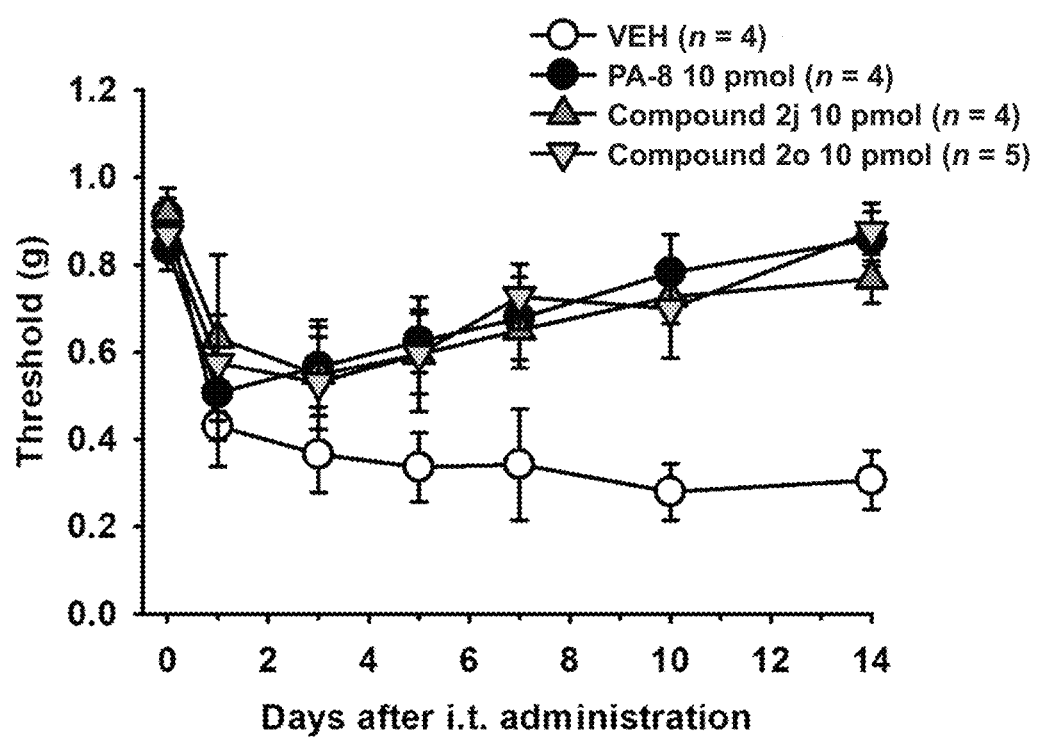
FIG. 5A shows the evaluation of drug efficacies (the effects of suppressing mechanical allodynia induced by PACAP intrathecal administration) using mouse pain models.
Figure 5B:
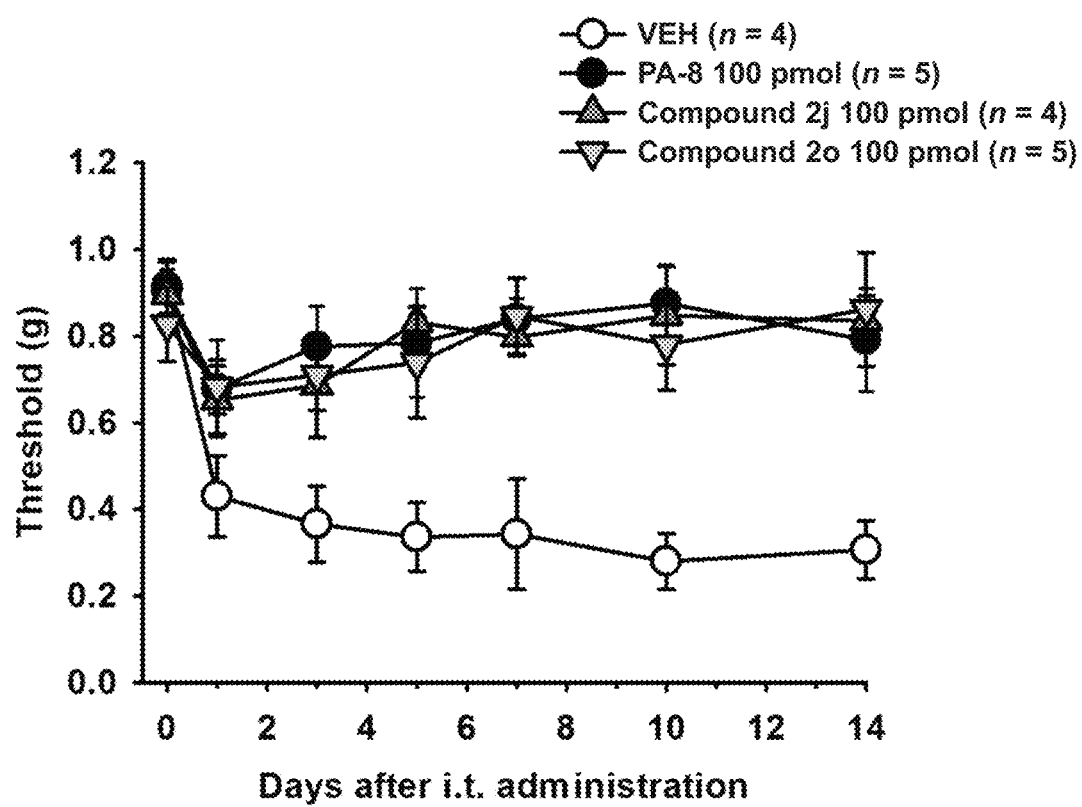
FIG. 5B shows the evaluation of drug efficacies (the effects of suppressing mechanical allodynia induced by PACAP intrathecal administration) using mouse pain models.
Figure 5C:
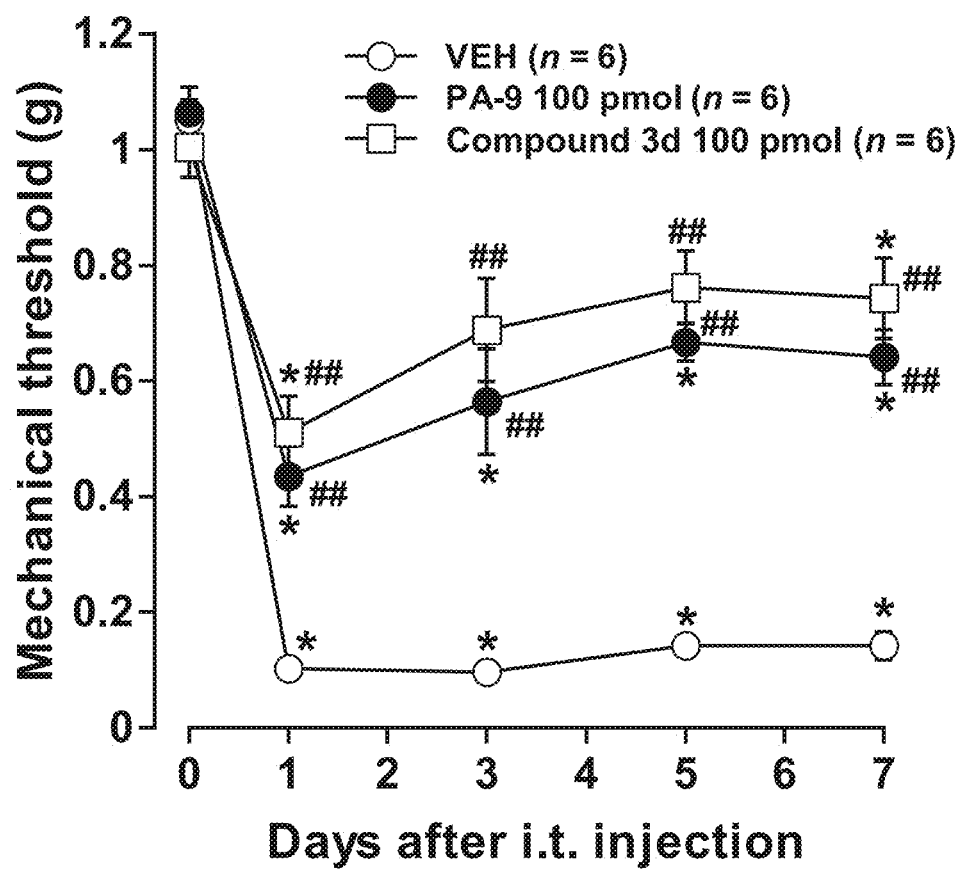
FIG. 5C shows the evaluation of drug efficacies (the effects of suppressing mechanical allodynia induced by PACAP intrathecal administration) using mouse pain models.

When single i.t. administration of PACAP (100 pmol/5 L) to mouse was performed, mechanical stimulus sensitive phenomenon (mechanical allodynia) occurred over a long period of time (for at least three months after the administration) (Non Patent Literature 1). The occurrence of this long-term mechanical sensitive phenomenon induced by PACAP was strongly suppressed by simultaneous i.t. administration of PA-8, the compound 2j or the compound 2o (10 or 100 pmol, FIGS. 5A and B); or PA-9 or the compound 3d (100 pmol, FIG. 5C). The mechanical sensitive phenomenon induced by PACAP was not suppressed in an example in which a solvent (VEH: 0.2% DMSO-containing artificial cerebrospinal fluid) was used instead of the compounds.

Male ddY mice (6 to 12 weeks old) were used, and the threshold to a mechanical stimulus was evaluated by the vonFrey test. Specifically, the 50% withdrawal reflex threshold (Threshold) was calculated in accordance with the method of Chaplan et al. (Chaplan et al., J. Neurosci. Meth. 53, 55-63, 1994). Each compound was dissolved in 99.7% DMSO, and then the resulting solution was diluted with an artificial cerebrospinal fluid for preparation (final concentration of DMSO was 0.2%).

[Example 6] Drug Efficacy Evaluation 3-1 Using Mouse Pain Model (Neuropathic Pain Model Associated with Cancer Chemotherapy: Cold Allodynia Induced by Oxaliplatin)

Figure 6:
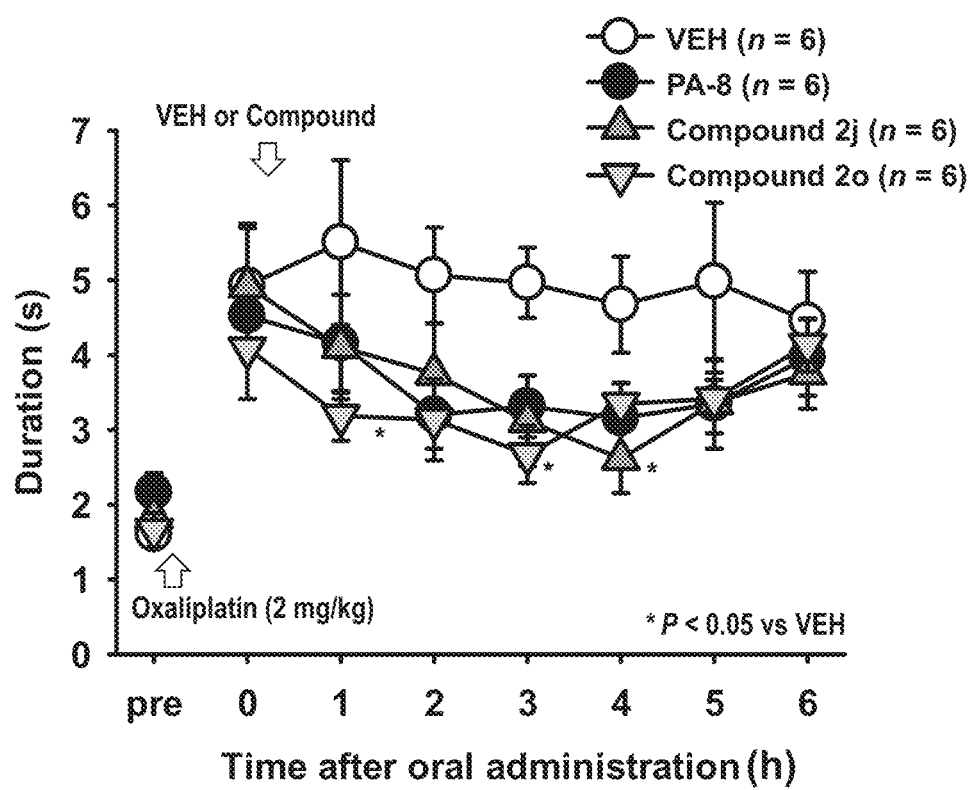
FIG. 6 shows the evaluation of drug efficacies (the effects of suppressing cold allodynia induced by oxaliplatin) using mouse pain models.

Oxaliplatin was dissolved in 5% glucose-containing saline and intraperitoneally administered at a dose of 2 mg/kg. A drug was administered on the fourth day after oxaliplatin administration. Male ddY mice (6 to 12 weeks old) were used. The axis of ordinates is the duration of the behavior of licking and paw waving after the application of an acetone drop (10 L) to the footpad of a hind paw. Although a solvent (VEH: 100% DMSO aqueous solution) had no effect, PA-8, the compound 2j and the compound 2o (10 mg/kg, single oral administration) each suppressed cold allodynia by oxaliplatin significantly over 4 to 5 hours, and the compound 2o was effective from an earlier period of time (the first hour after administration) (FIG. 6).

[Example 7] Drug Efficacy Evaluation 3-2 Using Mouse Pain Model (Neuropathic Pain Model Associated with Cancer Chemotherapy: Cold Allodynia Induced by Oxaliplatin)

Figure 7:
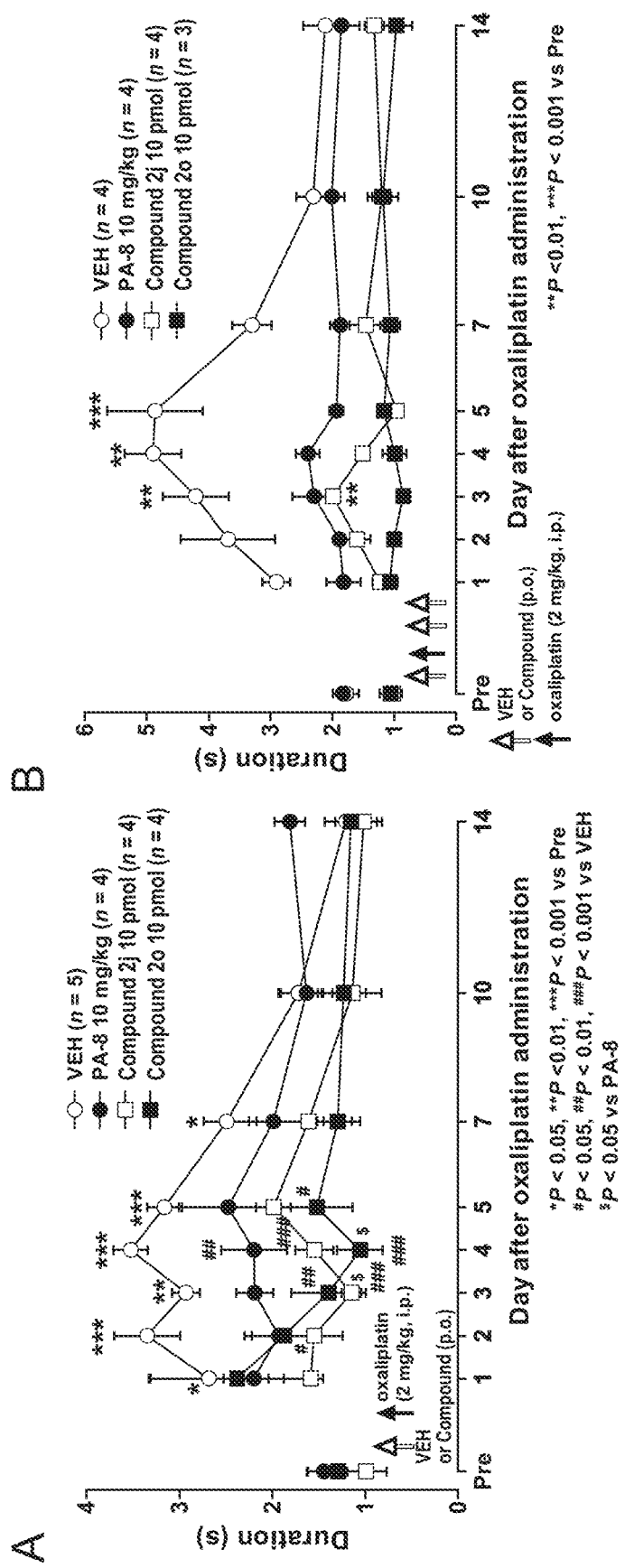
FIG. 7 shows the evaluation of drug efficacies (the effects of suppressing cold allodynia induced by oxaliplatin) using mouse pain models.

Oxaliplatin was dissolved in 5% glucose-containing saline and intraperitoneally administered at a dose of 2 mg/kg. Drug administration (oral administration) was performed 30 minutes before oxaliplatin administration (FIG. 7A); or 3 times: 30 minutes before oxaliplatin administration, 2.5 hours after the administration, and 5.5 hours after the administration (FIG. 7B). Male ddY mice (6 to 12 weeks old) were used. The axis of ordinates is the duration of the behavior of licking and paw waving after the application of an acetone drop (10 μL) to the footpad of a hind paw. Although a solvent (VEH: 10% DMSO aqueous solution) had no effect, PA-8, the compound 2j and the compound 20 (10 mg/kg) each suppressed the onset of cold allodynia by oxaliplatin significantly, and three administrations of the compound 20 suppressed the onset almost completely (FIG. 7B).

[Example 8] Drug Efficacy Evaluation 4 Using Mouse Pain Model (Peripheral Neuropathic Pain Model: Mechanical Allodynia Induced by Spinal Nerve Injury)

Figure 8:
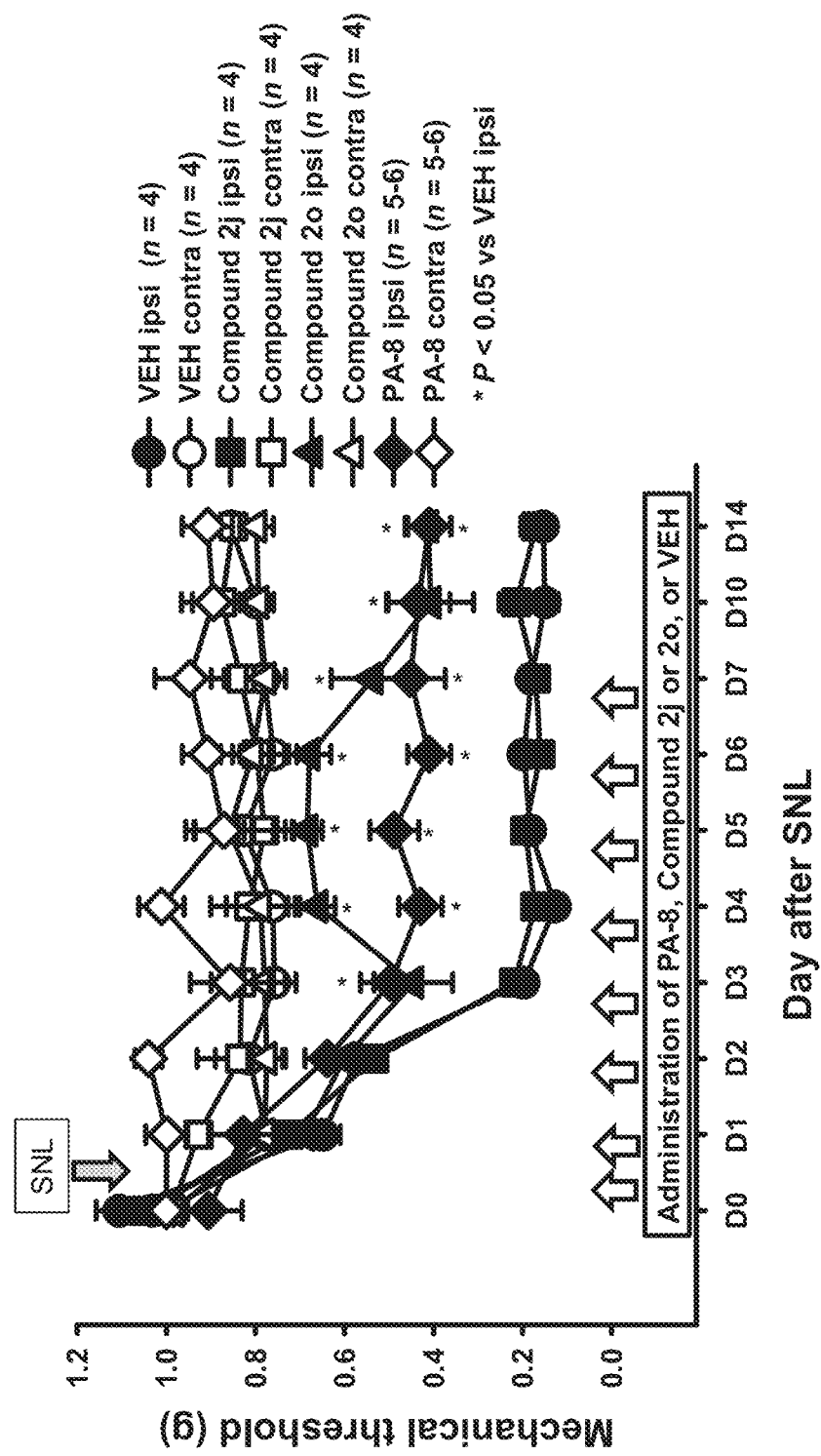
FIG. 8 shows the evaluation of drug efficacies (the effects of suppressing mechanical allodynia induced by spinal nerve injury) using mouse pain models.

Spinal nerve ligation (SNL) models in which the fourth lumbar cord spinal nerves of male ddY (6 to 12 weeks old) were ligated with silk thread were used. A solvent (VEH: 10% DMSO-containing saline). PA-8, the compound 2j or the compound 20 was intraperitoneally administered (30 mg/kg) 5 to 10 minutes before the ligation, and once a day for 7 days thereafter. The method of causing a mechanical stimulus is the same as that of Example 5, and data from the first day after the ligation (D1) are data 1 hour after the administration of VEH or the drugs. The compound 2j did not suppress the onset of mechanical allodynia as in the VEH group. Meanwhile, although PA-8 suppressed the onset of mechanical allodynia significantly, the compound 20 suppressed the onset of mechanical allodynia still more strongly, and maintained the mechanical threshold at a level equivalent to an uninjured side. As for PA-8 and the compound 2o, even though the administration was discontinued on the seventh day, the compound maintained the mechanical threshold highly significantly for at least 7 days thereafter as compared with the VEH group (FIG. 8).

[Example 9] Drug Efficacy Evaluation 5 Using Mouse Pain Model (Peripheral Neuropathic Pain Model: Mechanical Allodynia Induced by Spinal Nerve Injury)

Figure 9:
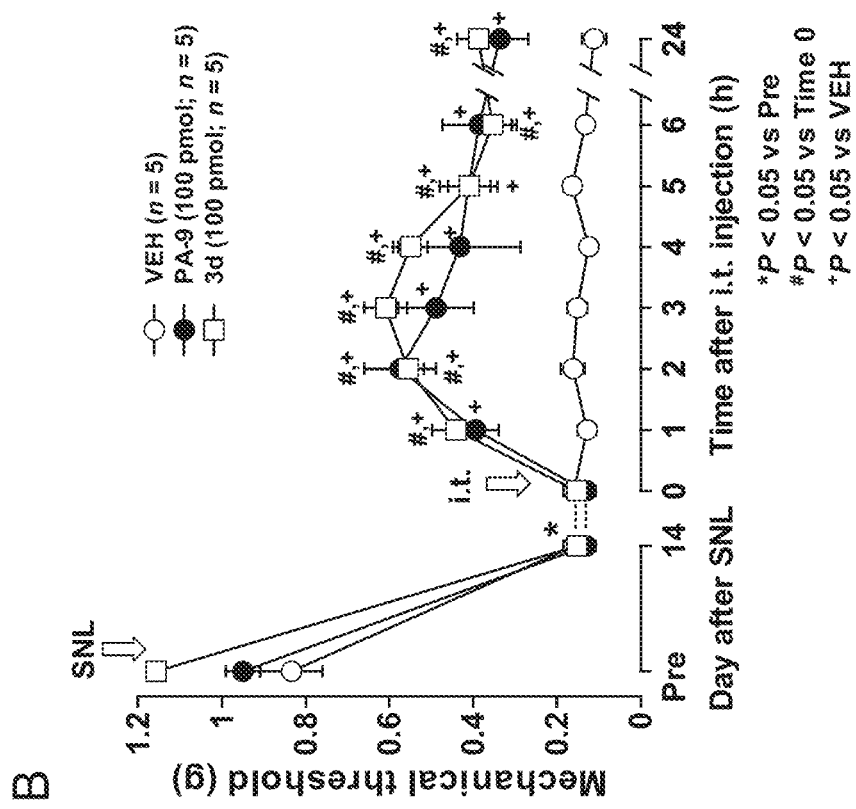
FIG. 9 shows the evaluation of drug efficacies (the effects of suppressing mechanical allodynia induced by spinal nerve injury) using mouse pain models.
Figure 9:
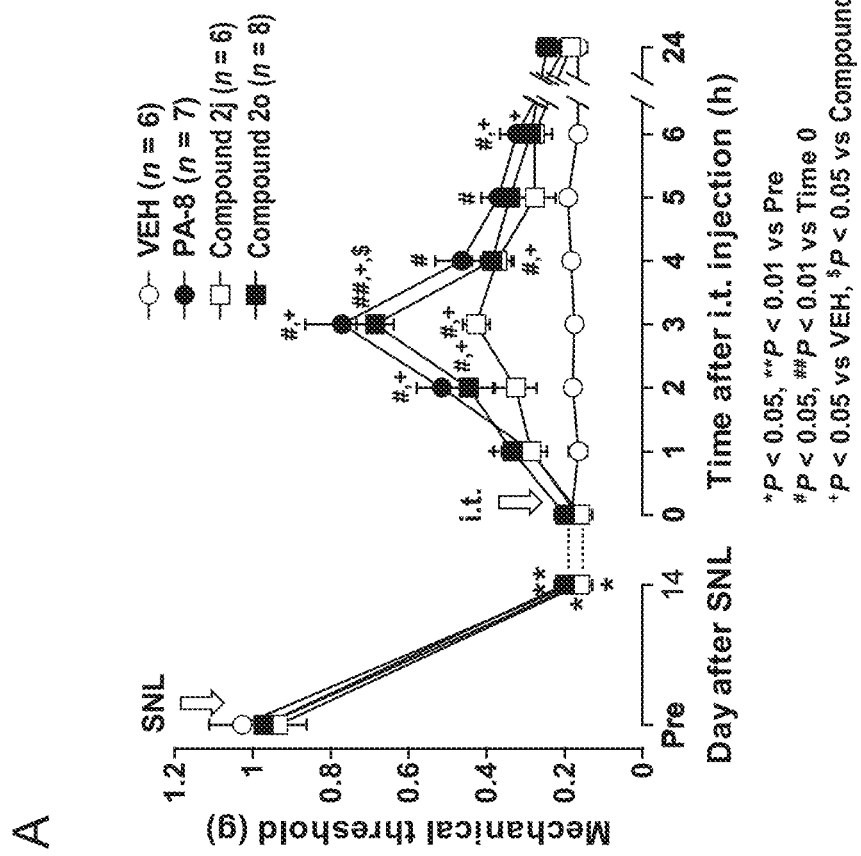

Spinal nerve ligation (SNL) models in which the fourth lumbar cord spinal nerves of male ddY (6 to 12 weeks old) were ligated with silk thread were used. The i.t. administration of a solvent (VEH: 10% DMSO-containing saline), PA-8, the compound 2j or the compound 2o (FIG. 9A), or PA-9 or the compound 3d (FIG. 9B) was performed on the 14th day after the operation. The method of causing a mechanical stimulus is the same as that of Example 5, and data were acquired for 24 hours after i.t. administration over time.

Although PA-8, the compound 2o and the compound 2j (100 pmol each) suppressed the onset of mechanical allodynia significantly, the maximum effect of the compound 2j (3 hours after the administration) was significantly inferior as compared with the compound 2o. PA-9 and the compound 3d (100 pmol each) also exhibited an anti-mechanical allodynia effect equivalent to PA-8 and the compound 2j, and also maintained the mechanical threshold highly significantly 24 hours after the administration.

[Example 10] Drug Efficacy Evaluation 6 Using Mouse Pain Model (Pain-Like Behavior Induced by Formalin)

When formalin is subcutaneously injected into a hind paw of a mouse, the animal exhibits pain-like behavior such as licking or brandishing the injected hind paw. This behavior exhibits two phases. The first phase is direct action of formalin on sensory nerves (to around 10 minutes after formalin administration). In the second phase (from around 10 minutes to 60 minutes after formalin administration), hypersensitization formed in spinal dorsal horn cells during the first phase (a type of plastic phenomenon in the nervous system also called central sensitization) is a main cause, and inflammatory reaction at the site of formalin administration contributes importantly.

Figure 10:
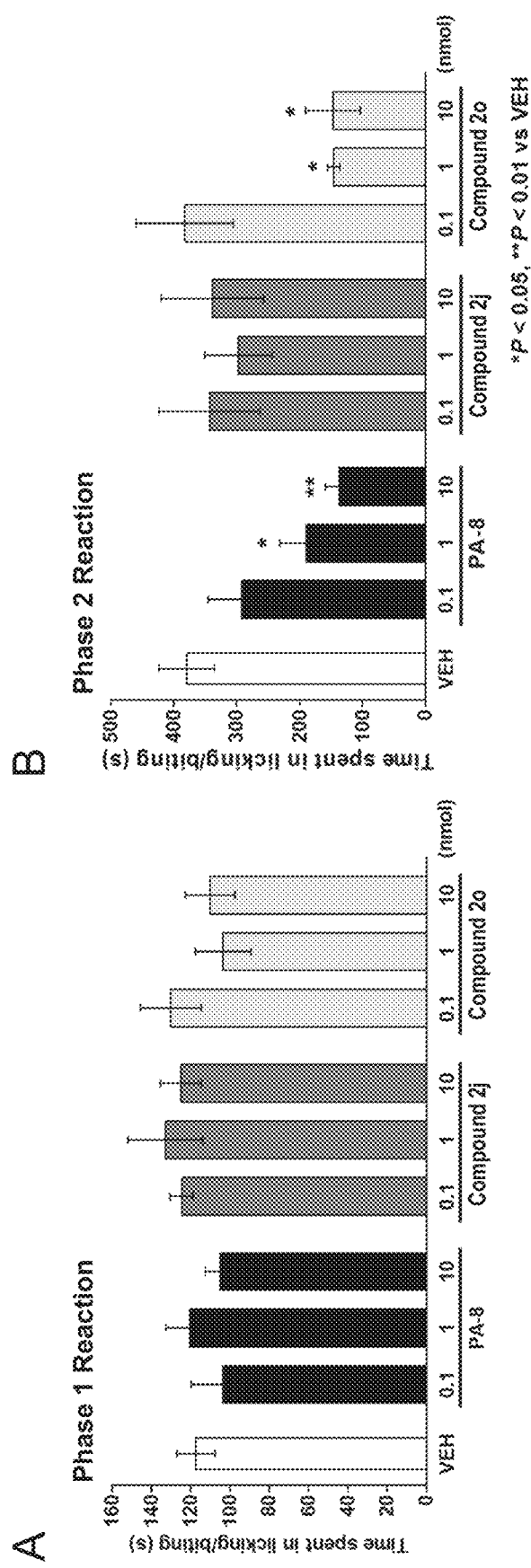
FIG. 10 shows the evaluation of drug efficacies using mouse pain models.

The i.t. administration of PA-8, the compound 2j or the compound 2o (0.1 to 10 nmol) did not affect the first phase reaction (FIG. 10A). Meanwhile, although PA-8 and the compound 20 suppressed the second phase reaction significantly depending on the concentration, the compound 2j did not affect the second phase reaction.

All publications, patents, and patent applications cited herein are incorporated herein by reference in their entirety.

REFERENCE SIGNS LIST

VEH (Vehicle) Solvent
ipsi ipsilateral
contra contralateral

The invention claimed is:

1. A compound represented by the following formula (I),

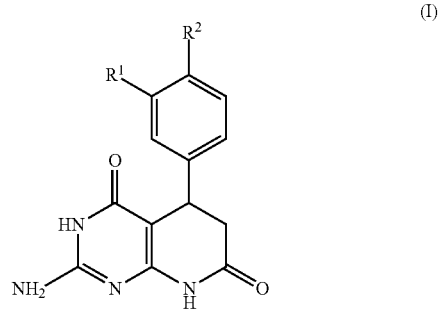

wherein $R^1$ is a $C_{1-6}$-haloalkoxy group; and $R^2$ is a hydrogen atom; or a salt thereof, or a solvate thereof.

2. The compound according to claim 1 or a salt thereof, or a solvate thereof, wherein $R^1$ is a trifluoromethoxy group in the formula (I).

3. An analgesic drug comprising a compound according to claim 1, a salt thereof, or a solvate thereof.

* * * * *